(12) United States Patent
Dunlap

(10) Patent No.: US 8,577,616 B2
(45) Date of Patent: Nov. 5, 2013

(54) SYSTEM AND METHOD FOR PLANT IDENTIFICATION

(75) Inventor: Susan C. Dunlap, Melon Park, CA (US)

(73) Assignee: Aerulean Plant Identification Systems, Inc., Menlo Park, CA (US)

( * ) Notice: Subject to any disclaimer, the term of this patent is extended or adjusted under 35 U.S.C. 154(b) by 1364 days.

(21) Appl. No.: 11/015,760

(22) Filed: Dec. 16, 2004

(65) Prior Publication Data

US 2005/0192760 A1    Sep. 1, 2005

Related U.S. Application Data

(60) Provisional application No. 60/530,359, filed on Dec. 16, 2003.

(51) Int. Cl.
| | | |
|---|---|---|
| *G01N 33/48* | (2006.01) | |
| *G01N 31/00* | (2006.01) | |
| *G06G 7/48* | (2006.01) | |
| *G06G 7/58* | (2006.01) | |

(52) U.S. Cl.
USPC .................... 702/19; 702/22; 703/11; 703/12

(58) Field of Classification Search
None
See application file for complete search history.

(56) References Cited

U.S. PATENT DOCUMENTS

| | | | |
|---|---|---|---|
| 5,253,302 A * | 10/1993 | Massen .......................... | 382/110 |
| RE36,041 E | 1/1999 | Turk et al. | |
| 6,137,896 A | 10/2000 | Chang et al. | |
| 6,292,575 B1 | 9/2001 | Bortolussi et al. | |
| 6,563,023 B2 | 5/2003 | Liu et al. | |
| 2002/0107959 A1 * | 8/2002 | Shteyn ........................ | 709/225 |
| 2003/0059124 A1 | 3/2003 | Center, Jr. | |
| 2003/0123713 A1 | 7/2003 | Geng | |

FOREIGN PATENT DOCUMENTS

WO    WO 03/050287    *    6/2003

OTHER PUBLICATIONS

United States Department of Agriculture, Natural Resources Conservation Services, National Plant Data Center, The Plant Database, News, Additions, and Enhancements, Plants Profile (IDS), Plants Advanced (IDS), Image Gallery (IDS)—Distribution Update Module Unveiled, p. 5, Jul. 15, 2002;—Two Improvements were made to the Plant Profile, p. 5, May.*
Horgan et al., Computers and Electronics in Agriculture, 2001, 31, 191-199.*
Larson (USDA Forest Service, 1993, General Technical Report, RM-238, 1-100).*
Wang et al. (IEE Proc. Vis. Image Signal Process, Feb. 2003, 150(1), 34-43).*
(web site) National Resources Conservation Services, *Plant Database, The Plant Database, News, Additions and Enhancements, Plant Materials Publications*, 2003, USDA, USA.
Hickman, JC, ed., *The Jepson Manual, Higher Plants of California*, 1996, pp. Contents, 59, 60, 63-65, 910, 914, 915, University of CA Press, USA.

(Continued)

*Primary Examiner* — Larry D Riggs, II
(74) *Attorney, Agent, or Firm* — Moore Patents; Cynthia R. Moore; David Dreyfuss

(57) ABSTRACT

Methods of compiling a database of images of plant species and the use of the database to identify unknown plant species are described. Images of the apical complexes of the plant are obtained and stored in a database to allow a comparison of the apical complexes with unknown plant species. The invention provides a facile method for the identification of unknown or unidentified plant species.

25 Claims, 19 Drawing Sheets

(56) References Cited

OTHER PUBLICATIONS

Lanner, RM, *Conifers of California*, 1999, pp. iv—vii, 262-265, 114-117, Cachuma Press, USA.

Symonds, GWD, *The Shrub Identification Book*, 1963, pp. 9, 20-27, 236, William Morrow & Co., USA.

Andrews, S et al., *Shrubs & Climbers*, 1996, pp. Contents, 8-9, Dorling Kindersley, Ltd., UK.

Brenzel, KN, ed. *Sunset Western Garden Book*, 2001, pp. Contents, 266, Sunset Publishing Corp., USA.

(web site), *Plant Information Center*, 2003, www.ibiblio.org/pic/herbarium.htm, U. North Carolina—Chapel Hill, USA.

(web site) *Dendrology*, 2003, www.cnr.vt.edu/dendro/dendrology.html, 2003, Virginia Tech, USA.

Old, R, *1000 Weeds of North America*, (CD) 2003, XID Services, USA.

*Ex Parte Susan C. Dunlap*, BPAI Decision on Appeal, Appeal No. 2011-005298, 2012.

\* cited by examiner

SYSTEM AND METHOD FOR PLANT IDENTIFICATION

CROSS-REFERENCE TO RELATED APPLICATIONS

This application claims the benefit of priority from U.S. Provisional Application No. 60/530,359 filed Dec. 16, 2003. This application is hereby incorporated by reference for all purposes.

BACKGROUND OF THE INVENTION

1. Field of the Invention

The present invention relates to a process for compiling a database of plants, and the use of the database for the identification of plant species and genera. In one aspect of the invention, the process is based on the characteristics of the plant's apical complex. The present invention also relates generally to methods and apparatus for providing search results in response to a search query provided by a user.

2. Description of Related Art

A long-standing problem that has frustrated anyone seeking to identify an unknown plant specimen using traditional resources is the inability to simply and accurately identify the plant species and its genus based on the specimen's physical traits.

Presently, there are limited methods for identifying a plant species. One common method of identifying a plant species include the use of the internet to search through various electronic databases. However, websites containing these relatively limited databases are generally designed to provide information relating to a known species of a plant, and therefore, one must have prior knowledge of the species in order to use the databases effectively. For a novice who is unfamiliar with plant identification or botanical terminology, there are many obstacles for searching the database. Therefore, without the knowledge of additional botanical terms beyond the simple description of a plant specimen, such as a leaf or a flower, it may be difficult to perform an effective search in order to identify the plant genus or the plant species.

Another common method of identifying a plant is with the use of literary sources, such as texts and encyclopedia that document various plant species. Although the publications may include pictures, photographs and descriptions of a plant, there are no systematic documentations or procedures established among the publications.

Similarly, there exists various methods, apparatus and systems for uniquely identifying human individuals by their particular physical characteristics, such as the individual's unique finger prints, palm prints, iris, facial features, or combinations thereof. For example, particular facial parameters such as the distances between identifiable points on the human face, and/or ratios of the facial parameters may be used to identify an individual as the parameters for each individual are unique. Particular parameters such as the distance between the eye retinae, the distance from each eye retinae to the nose bottom and to the mouth center, and the distance from the nose bottom to the mouth center are set forth. The technologies have been disclosed in U.S. Pat. No. 4,975,969 and references cited therein.

In addition, standard methods known in the art that are used for the identification of unidentified plant species utilizes one's ability to distinguish particular characteristics of the plant's leaves, stems, flowers, seeds, and roots. However, none of those provides a omnipresent, definite and unique identifying characteristic for identifying the plant species.

Therefore, there is a need for establishing a systematic method for compiling a database of plant species to assist in the identification of unidentified or known plants for both novices and experts in the field.

SUMMARY OF THE INVENTION

The present invention provides solutions for at least some of the drawbacks discussed above. Unlike the text-based system in current use, embodiments of the present invention will create a visual plant identification system that can be used by a wide audience, including non-experts mystified by botanical nomenclature. Fewer than 10% of the plants in cultivation are represented by photographs in the current visual literature, and these photographs are generally not designed to assist in the determination of a plant's identity.

Neither the text-based nor the visual systems available enable a blind search within the potential vegetative inventory and cannot be easily used to manage information. This inability has created a deficiency in the industry and the industry have responded to this deficiency by actively limiting the diversity of plants in cultivation at any one time. It is estimated that only 3% of the potential inventory is available at any one time and the available market has become constricted. The ease of use of the present system will help horticulturists overcome the current disadvantages associated with having to deal with a tremendous number of species and enable commercial users to expand their products and businesses.

In one embodiment, the present invention provides a method for compiling a database of plant species. Known plant species are obtained, and the image containing specific characteristics of the plant, including the apical complexes of the plant are obtained. The image data of the plants are correlated and stored in a database. The database may be used to create an identification system useful to plant retailer, plant wholesalers, academics, scholars, researchers, librarians, and collectors.

In another embodiment, the invention discloses a general method for the identification of unidentified plant species by using various methods to compare specific features of the plant characteristics, include the features of the plants' apical complexes, with that of known plant samples, databases, and references.

The invention further relates to a method for the identification of unidentified plant species using a database compiled by the present invention. Specifically, samples or images of unidentified plant species are obtained, and the samples or images are compared with the database of known plant species having distinct characteristics to identify and match the unidentified plant with plants species from the database. Various methods disclosed for the identification of the unidentified plants include the use of optical recognition software, image scanning systems, software driven text and image algorithm, the application of multiple dichotomous keys and morphology, data manipulation, including digitized Fourier transform, and various electronic search, compare and matching systems.

In a particular embodiment, the identification of unidentified plants, or plants that are considered to an individual to be unknown or unidentified, is accomplished by scanning at least one particular or unique characteristic of the unidentified plant using a scanner, inputting the scanned image into a computer, and using a computer based algorithm, search a database of plants having unique characteristics to identify the unknown or unidentified plant genus and/or species. In one particular variation, the scanner is a portable scanner that may be taken into the field. In another particular variation, the unique characteristic of the plant is the plant's apical complex. In another particular variation, the unique characteristics of the plant is the apical complex and at least one other unique or distinguishing characteristic of the plant.

In the above variation, the computer algorithm analyzes and searches the plant's unique features or characteristics, such as the plant's apex, spine, epidermis, flowering eye, leaf, peduncle, prickle, rib, stem, or combinations thereof. For example, the particular plant parameters such as the distances between identifiable points on the plant and/or the apical complex, and/or ratios of the plant's parameters may be used to identify the unidentified plant as the parameters for each plant are unique. Particular parameters such as the distance between the spine and peduncle, the distance from each spine to the peduncle and to the flowering eye, and the distance from the spine to the flowering eye are set forth. Similarly, the use of this method for the identification of individuals by their unique facial features has been disclosed in U.S. Pat. No. 4,975,969 and references cited therein.

It should be understood that in one aspect of the present invention, a system may be presented that uses photographs to generate biometric data. Biometrics is the science and technology of measuring and statistically analyzing biological data. Biometrics is the defining feature of facial recognition software and hardware; it simulates brain activity by interpreting complex visual patterns for purposes of identification by noting the relative distances between features and groupings of features. The present invention may define these groupings as trait clusters. By taking pictures of a plant's apical complex and standardizing the method in which these picture are captured, the images can be used to generate biometric data which is then used to compile a database. A photograph of a plant's aerial trait cluster has measurable features that can be statistically analyzed by measuring the relationship between traits. The presence of a single trait may significantly narrow the list of possible species in a plant search (just as an iris with a spec of brown in it is sufficient to distinguish a human individual). In one embodiment, biometrics only apply when the data is collected using rigorous visual standards.

One object of the present invention is to establish systematic standards in the horticulture field for capturing images to generate biometric data such but not limited to identification purposes. One method is to gather systematic photographs of a plant's aerial trait cluster. These photographs can be used or processed to generate biometric data. As with facial biometrics, the present system may ultimately yield the accurate identification of an individual—in the present case a plant species rather than a human species. Broad categories in botany (tree, bush, vine, etc.) are a novice's version of a trait cluster.

It should be understood that the present invention may combine the photographs with original plant keys, specifically designed to take advantage of the biometric data. In botany there is an acute need to define one's terms. The present invention mitigates this problem by generously illustrating these terms with photographs. Embodiments of the present invention may combine all of the above methodologies to create a new system of identification. "Most advances in Science have to do with an improvement in resolution." *Visual Displays of Quantitative Information* (Edward Tufte) and the present invention has done this for botany.

Embodiments of the present invention may provide visual aids and photographs that are interactive. The user can search while referring to the visual aids. Text searches of the present invention may be toggled to accompanying and informative visual aids. The user navigates through the plant family via photographs and text. The primary embodiment of the system is photo-driven; however, it is possible for an advanced user to skip ahead using the text window. For most users, the system uses images to verify text-based traits at each point along the search. The users options or selection are presented in both text and images. Most criteria in known systems are very technical, and, lacking photographic reference, require too much from the novice user (e.g., the user needs to select from a variety of leaf arrangements in order to proceed). The present invention does not require the user to be informed about multiple, unrelated, glossary terms or sort criteria—it will have isolated the term one needs to know in order to navigate further in a search.

The present invention may isolate the user from sort criteria unrelated to a specific search. In one embodiment, only plant traits which will narrow the number of possible apical complex views will be asked. The proprietary aerial trait-cluster provides sufficient additional data to waive other distinguishing traits. As a nonlimiting example, some embodiments may pose initial questions about the habit of the plant or growth trait clusters. The questions posed to the user will be based on the user's response to previous questions and will narrow the possible matches until only comparisons of apical views remain. In one embodiment of the invention, the final matches are based only on apical complex features.

In yet another embodiment, the present invention provides an image database of plant images. In specific embodiments, the images contain at least one apical view of each plant in the database. The images may be used to find or confirm the identity of unknown plants. The images are created by a standardized method so that biometric data may be obtained from the image. Visual data and text data may be linked so that they are viewed concurrently. The apical view allow for the design of better text keys. This may allow the user to generate text keys based off of an apical view driven system.

These apical views may generate biometrics based on trait clusters. The images generate a complex pattern. The present invention may be used to standardize way the pattern captured. Biometrics are based on scanning the images and generating image metrics. All the data needed is in the image. This inventions narrowed the number of traits to consider, because in one embodiment, the final matches are based on traits found when comparing view of the apical complex. Embodiments may use actual images since they contain more information. Although not limited to just image, line drawings are filtered data and may not convey the same level of detail as images.

Additional objects, features and advantages of the invention will be set forth in the description which follows, and in part, will be obvious from the description, or may be learned by practice of the invention. The objects, features and advantages of the invention may be realized and obtained by means of the instrumentalities and combination particularly pointed out in the appended claims.

A further understanding of the nature and advantages of the invention will Become apparent by reference to the remaining portions of the specification and drawings.

DESCRIPTION OF THE SPECIFIC EMBODIMENTS

It is to be understood that both the foregoing general description and the following detailed description are exemplary and explanatory only and are not restrictive of the invention, as claimed. It may be noted that, as used in the specification and the appended claims, the singular forms "a", "an" and "the" include plural referents unless the context clearly dictates otherwise. Thus, for example, reference to "a processor" may include multiple processors, and the like. References cited herein are hereby incorporated by reference in their entirety, except to the extent that they conflict with teachings explicitly set forth in this specification.

Figure 1:
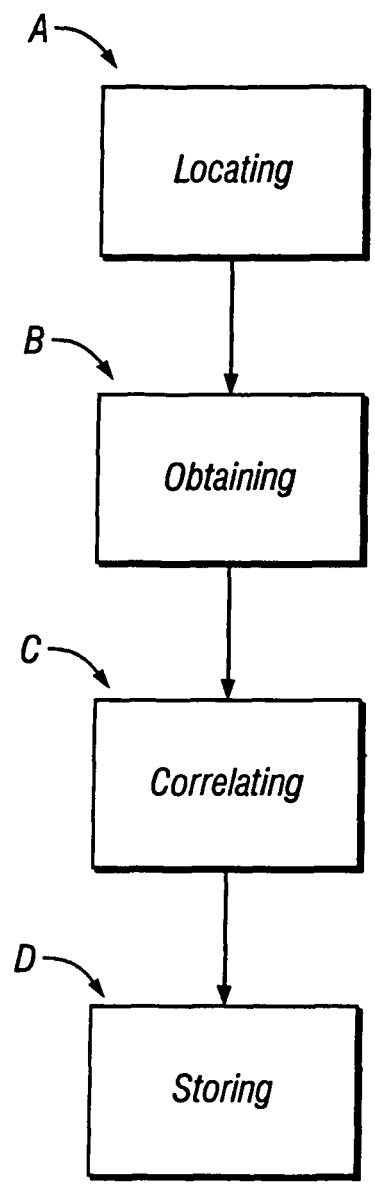
FIG. 1 shows a flow chart for one embodiment of the present invention.

With reference to FIG. 1, in one embodiment, the present invention provides for compiling a database of a plant genus for the identification of plants, comprising: (A) locating a stem and/or branch apical complex of the plant; (B) obtaining an image of the plant's distinguishing characteristics and the distinguishing characteristics of the apical complex with sufficient resolution to distinguish among information corresponding to the plant species; (C) correlating the plant species image with unique identification responding to the plant species; and (D) storing the plant image and identification information in a database.

In one variation, the unique identification information of the plant comprise of the plant's distinguishing characteristics and the plant's genus and species.

In another variation, the database contain distinguishing characteristic information corresponding to the plant species, and the plant genus. In another variation, the database comprises a plurality of records having a number of data fields, where the database is stored in a computer-readable memory. In one particular variation, the images of the apical complex are photographic images. In one variation of the invention, the images are magnified. In another variation of the invention, the images are obtained at a magnification of about 2 times to about 10 times actual size or magnification.

In one variation of the process, the above Step (B) further comprises obtaining the longisectional images of the apical complex. In another variation, the longisectional images are obtained at least about 50 to about 100 times magnification. In one particular variation of the invention, the plant's distinguishing characteristics comprises the presence or absence of excessive soil moisture, tendrils or graspers, a twining habit, a trunk or vertical stem, feather-like leaves (fronds), fly trap, hinged, pitcher-shaped or sticky tentacular leaves, complex, showy flowers, aerial or exposed roots, sympodial or monopodial habit, center-folded leathery lance-shaped green leaves, leafless, thick, fleshy stem, spines and/or areoles, regularly spaced nodes or joints, a hollow stem, sheath(ing) leaves, multiple stems emanating from the plant's base, herbaceous leaves on a soft-wooded plant, woody stems, pinnate or palmately cleft (palm) leaves, a main stem or trunk with a crown of palm leaves, or a main stem or trunk. This process allows positive identification of plants using the plant's unique characteristics.

In another particular variation, the distinguishing characteristics of the apical complex identified comprises the growth pattern of the apical complex selected from a member of the group consisting of the size, shape, color, presence or absence of the apical complex feature, position of the feature, geometrical dimension, flower, texture, a relationship thereof, and a combination thereof.

In a further variation, the distinguishing characteristic of the apical complex comprises the shape of the apex, presence of a spine, color of the spine, position of the spine, angle of the spine, size of the spine, presence of a spine shield, color of the spine shield, shape of the spine shield, length of the spine shield, color of an epidermis, shape of the epidermis, shape of a flowering eye, position of the flowering eye, presence of a leaf, position of the leaf, size of the leaf, shape of the leaf, color of the leaf, presence of a leaf scar, size of the leaf scar, shape of the leaf scar, color of the leaf scar, presence of a peduncle, position of the peduncle, size of the peduncle, frequency of the peduncle, presence of a prickle, position of the prickle, size of the prickle, texture of the prickle, presence of a rib, number of ribs present, depth of the rib, edge feature of the rib, width of the rib, contour of the rib, width of the spine shield relative to the width of the rib, shape of a stem, presence of a tubercle, size of the tubercle and shape of the tubercle or combinations thereof.

In each of the above variation, the apical complex of the plant shows at least one growth cycle. Further, the invention teaches that in each of the above variation, the apical complex of the plant shows at least three growth cycles.

In another embodiment, the invention teaches a process for identifying unidentified plant species comprising: (A) obtaining a sample or image of the distinguishing structures and apical complex of the plant to enable identification of at least one distinguishing characteristic typical for the species or genus; (B) comparing the distinguishing characteristics with a database of at least one plant genus derived from a plurality of images of distinguishing characteristics of apical complexes typical for each plant in the plant genus, the distinguishing characteristic of the plant to be identified being sufficient to enable identification of the plant within the genus; (C) identifying a distinguishing characteristic of the apical complex typical for the species and correlating the distinguishing characteristic of the apical complex with a known and identified plant species; and (D) repeating step (C) for a second and subsequent distinguishing characteristics until a sufficient number of the distinguishing characteristics of the apical complex have been ascertained to correlate the apical complex with the plant species, and (E) assigning the plant to a plant genus and/or genus with similar distinguishing characteristic of the apical complex.

In one variation of the above embodiment, the information comprising the identified plant species, genus, distinguishing characteristics, and the image of the plant are stored in a database.

In another variation, the distinguishing characteristic comprises of the patterns or number of patterns of the apical complex for the plant.

Although the distinguishing characteristics for the above embodiment is applicable to a large number of different types of plants, in one particular variation, the plant is a vascular plant. In a particular variation, the vascular plant is selected from the group consisting of the Euphorbia genus and Portulacaceae, the Cactaceae, Crassulaceae, Aloeaceae and Lilaceae families.

In one variation, the plant's information is stored in searchable format in response to a specific query in order to identify the specific plant that satisfy the characteristic of the query criteria. In one variation of the above process, the process of identifying a plant employs a software algorithm to identify unknown or unidentified plant. In another variation of the above process, the software driven identification process uses guided text with complementary visual images to guide the user and assist the user to identify unknown or unidentified plants.

In yet another variation the present invention further teaches the process of comparing the distinguishing characteristics of the plant and employs dichotomous keys that are based on physical attributes of the plants. In another variation of the invention, the process of comparing the distinguishing characteristics of the plant employs dichotomous keys that are based on plant morphology. In yet another variation, the process of identifying unidentified plants utilizes the plant's morphology, distinguishing or unique characteristics, and the relative positions or distances of the characteristics to at least one of the plant's distinguishing features.

In one particular variation, the process of comparing and matching the distinguishing characteristics of the plant employs optical recognition software and image scanning systems. In a further process of the invention, the process of comparing and matching the distinguishing characteristics of the plant uses a search engine. Similar systems for performing biometric security by analyzing and comparing an image of a person's face is disclosed in U.S. Reissue Pat. No. 36,041, entitled, "Face Recognition System," issued to Turk et al., and is hereby incorporated by reference.

In each of the above processes as taught herein, the process of comparing and matching is made from two or three-dimensional images. A method of automatically recognizing a human face by developing a three-dimensional model of a face; and generating a number of two-dimensional images based on the three-dimensional model, and searching from the database of an input images is disclosed in U.S. Patent Publication No. 20030123713. In addition, U.S. Patent Publication No. 20030059124 discloses a system and method for acquiring, processing, and comparing an image with a stored image to determine if a match exists. The system correlates the acquired image with the set of stored images and provides the best matches for application in facial recognition systems in real time. Three dimensional techniques developed for comparing two dimensional images with three dimensional images for facial recognition applications are disclosed in U.S. Pat. No. 6,137,896. U.S. Pat. No. 6,292,575 discloses a system and method for acquiring, processing, and comparing an image with a stored image to determine if a match exists for application in facial recognition.

In another variation of the invention, the two or three dimensional images are black and white or color images.

In one variation, the above database is obtained from the process of as taught herein above. There is also provided a method and apparatus for uniquely identifying an unidentified plant.

In one embodiment of the invention, the method for identifying an unidentified plant generally comprises: (a) via imaging at least one particular characteristic of the plant, obtaining at least one ratio of at least a first and second plant characteristic of the plant, the first characteristic parameter comprising the distance from a first identifiable location to a second identifiable location on the plant, and the second characteristic parameter comprising the distance from a third location on a selected structure of the plant to one of the first, second, and a fourth location on the plant; (b) storing values of said at least said ratio of said first and second plant characteristics of the plant in a database or storage medium; and (c) upon identifying the unidentified plant, obtaining at least one ratio of first and second plant characteristic of the plant, wherein the ratio corresponding to at least said ratio stored on the database or storage medium, and comparing the value of the stored ratio with the value of the ratio obtained of the unidentified plant. As used herein, the term "unidentified" means either that the plant is unidentified with respect to a particular user of the present invention, while the plant is known or previously identified by others and the identity of the plant is already stored in the database; or that the unidentified plant is an unknown plant or a plant that has never been identified by anyone. In the latter case, the present method allows the user to add or supplement the database with such a new species of the newly unidentified plant.

In another embodiment, the present invention provides a method and apparatus for identifying unidentified plants based upon computer matching of a region of interest in a computer image scan of the particular characteristics of the plant. In one embodiment, there is provided correlation techniques that may compare previously processed image information with a presently scanned image to confirm or generate the identity of un unidentified plant. In a further embodiment, the correlation technique correlates a sorted list of possible matches of known plant genus or species. The system can also sort the information by a previously defined class.

Definition:

Unless otherwise stated, the following terms used in the specification and claims shall have the following meanings for the purposes of this Application. The terms are also defined in the following texts: Vascular Plant Systematics, Radford, Dickison, Massey and Bell, 1976, Harper & Row, NY. The glossary may be found at ibiblio.org/botnet/glossary.html; Swartz, Dilbert, 1971, Collegiate Dictionary of Botany, NY, N.Y., The Ronald Press Company; Anderson, E. A., 2001, The Cactus Family, glossary, Oregon, Timber Press; Eggli, Urs, 1993.; Glossary of Botanical Terms; Surrey, England, British Cactus & Succulent Society; Brickell, C & Zuk, J, editors, 1997, The American Horticultural Society A-Z Encyclopedia of Garden Plants, glossary, NY, N.Y., DK Publishing; Stein, Jesse, Ed. Random House Dictionary of the English Language; The Unabridged Edition, 1966, N.Y.; Radford, Dickison, Massey, Bell, 1976, Vascular Plant Systematics, N.Y., Harper & Row; Pridgeon, A. ed, 1992.; The Illustrated Encyclopedia of Orchids, Oregon, Timber Press; Northen, R. T., 1962; Home Orchid Growing, N.Y., D. Van Nostrand Co., Inc.

"Apex" means the tip, the extreme end, the summit, the growing point of a stem, branch, or root.

"Apical complex". apical=At the tip or apex, at the summit, belonging to the apex or point. (Position) towards, at, near, etc. the end (apex, tip, etc.) of an organ. "Complex": a group of complicated or interwoven parts or fibers. b. a mosaic of communities determined by the local diversity and geomorphic factors and repeating itself or occurring in diverse localities. Thus the "apical complex" refers to a complicated group of interwoven parts found when the tip, apex, or summit of a stem, branch, or plant is viewed overhead; e.g., a top view of the crown of a tree, an overhead view of a sub shrub, and overhead view of a single branch of a shrub, or the magnified longisection of the tip of a stem. This complex and various details of the complex may be visualized in various magnifications such as but not limited to, magnified lenses for photographic or imaging equipment, or may be visualized using electron micrographs or other magnified microscopic methods.

"Apical growth" means an extension in the length of the axis at the apex only of a branch or stem.

"Apical meristem" means the meristematic cells at the tip of a stem or root from which the tissues of the mature axis are ultimately formed.

"Branch" refers to stem or limb growing from the trunk or main stem of a plant.

"Evergreen" means 1. having green foliage at all seasons, not deciduous, losing leaves at all seasons but never all of them at one time.

"Growth cycle" refers to a single growth period of a plant. A growth cycle of a plant may be observed in a plant as a layer of wood (for example, as an annual ring) that is produced during a single period of growth.

"Image" refers to a reproduction of the form of something, such as but not limited to, a plant or a specific characteristic of a plant. An image may be an optically formed duplicate or other representative reproduction of an object such as but not limited to, those obtained from taking photographs of an object. The reproduction may be obtained in one or more various forms, such as but not limited to, by a camera to produce a positive print or in digital format. The image may be an exact duplication of data in a file that is stored in a different medium.

"Keys" such as "verbal keys" or "visual keys" or "written keys" as defined in this application, refers to 1. a systematic tabular classification of the significant characteristics of the members of a group of organisms to facilitate identification and comparisons. 2. written keys also refers to a systematic tabular classification of the significant characteristics of plants to facilitate identification and comparisons using botany terminology and other useful terms. 3. visual keys also refers to a systematic tabular classification of the significant characteristics of plants to facilitate identification and comparisons using photographs, diagrams, drawings and other visual aids.

"Leafy rosette" means a rosette with herbaceous leaves.

"Longisection" means a composite term of the phrase "longitudinal section". Ideally a lengthwise section taken down the center of a stem or branch tip. Typically magnified to enlarge details exposed by the section.

"Meristem" means the undifferentiated formative or generative cells of plants which give rise to daughter cells capable of further division, the cells found in the cambium or growing points capable of further development.

"Peduncle" refers to the stalk of a flower cluster or of a solitary flower.

"Radial symmetry" means the symmetry of a plant body, organ, or tissue which may be divided into two equal parts in any number of planes.

"Rosette" means: a. a dense, flat, imbricated cluster of leaves growing from a short stem at the base of a plant, as a dandelion; b. a collection of leaves growing close together and radiating from the main stem.

"Stem" means the main ascending axis of a plant bearing leaves or flowers or both.

"Succulent" means 1. describing a plant that stores water in enlarged, specialized spongy portions such as but not limited to, leaves, stems, or roots; leaf succulent a plant that uses the (thickened) leaves to store water; a plant with fleshy leaves. 2. of a plant, having fleshy and juicy tissues. 3. showing succulence. 4. succulents may be loosely grouped as stem succulents (including cacti), leaf succulents, root succulents, and caudiciform succulents. Stem succulents (most of which are cacti) have swollen, moisture-retaining stems, usually slender, oval, columnar, or spherical in shape. They may be climbing, pendent, or tree-like in habit; some resemble flat, leaf-like pads. Epiphytic succulents native to dry regions often produce aerial roots on their stems that absorb moisture from the atmosphere. Cacti are distinguished from other stem succulents by their unique growing points, known as areoles. Most lack foliage . . . (and) have ribs. Along the ribs are the areoles. Leaf succulents have foliage but often lack a stem, whereas cacti and other stem succulents have a swollen stem but mostly lack leaves. In both types stems or foliage expand when water is plentiful and contract or, in the case of foliage, drop away, in a drought.

"Trait cluster" as used herein refers to the overall, species-specific vegetative pattern and a concentrated view of several characteristics of the plant.

"Tree" means 1. woody perennial with a crown of branches developing from the top of a usually single stem or trunk. 2. a perennial plant having a permanent, woody, self-supporting main stem or trunk, ordinarily growing to a considerable height, and usually developing branches at some distance from the ground. 3. a woody plant with one main trunk and a more or less distinctly elevated head.

"Vine" means 1. the stem of a climbing or trailing plant, e.g. the stems of many species of Cucurbitaceae, etc. 2. any plant having a long, slender stem that trails or creeps on the ground or climbs by winding itself about a support or holding fast with tendrils or claspers. 3. or liana: an elongate, weak-stemmed, often climbing annual or perennial plant, with herbaceous or woody texture.

Additional terms related to computer implemented methods according to the present invention may have the following definitions.

A "server" in a hardware configuration may be a computer such as a personal computer (PC) or other intelligent device. A server typically performs the bulk of the centralized or generalized tasks in the network and often has more memory, processing speed, and storage than the other device on the client-server network. Alternatively, the server may perform specialized tasks such as but not limited to, distributing electronic mail, data storage or printing. In the software arrangement, a "server" typically is a program that provides data, stores data, or provides some service to other programs to lo which the server is connected. A server may be a program with higher priority, greater memory, or greater capabilities compared to the other programs connected through the network. A server also may be a program that includes specialized capabilities or has higher priority with respect to certain tasks or functions.

A "client" in the software arrangement is generally a program used by a user. A program typically makes use of data, processing, storage, or other resources of another program. A client may be used to communicate with a source or destination through a higher priority, more powerful, more capable or different program. The client may run on a computer such as but not limited to, a personal computer (PC), intelligent device, personal digital assistant (PDA) or workstation used by a user. In use, the client may carry out tasks in the process of which the client may request information or otherwise may use the resources of another object such as the server or another client to accomplish such tasks.

EXAMPLES

The following examples are illustrative and not intended to be limiting of the invention.

Obtaining Images of Plant Species:

Various species of known or unidentified plants were collected. Different species of plants, including annuals, bulbs, grasses, groundcovers, perennials, scrubs, vines, and wildflowers were collected where feasible. Some species were photographed in the field. Others were brought to the studio—either as a whole plant or a branch cutting. Typically, when working in the field, the photographic equipment was brought to the plant. When photographing potted plants in the field, the plant may be brought to the photographic equipment set up at a central location.

Photographic images for various components, views and profiles were obtained for a particular plant specimen. Depending on the nature of the specimen, a complete plant profile may be obtained or only certain limited views or profiles of the specimen may be obtained. A complete plant profile was usually obtained when a specimen was determined to be a member of a genus in which limited data has yet to be obtained. The complete profile was usually taken of the unidentified plant so that the plant's unique traits or characteristics could clearly isolated and identified. Once the plant was identified, the data collection may be focused on those traits or combination of traits that may be useful in a database sort. In addition, a complete profile may be needed to confirm and cross-reference information from various sources of botanical literature, such as but not limited to, text or picture based references.

If a complete profile was desired, multiple photographs were taken of both the stem and any branches exhibiting a variety of growth characteristics. Variable growth characteristics may include various growing conditions or plant characteristics, such as but not limited to, whether the plant was dormant or under active growth.

The primary angle of the photographic images taken for the plant specimen was directly overhead of the stem apex and the branch apex.

Photographic images of the complete profile of the plant specimen may be obtained. The complete profile may include a side view image of the stem apex or the branch apex.

When a complete profile was sought and when photographing the plant in the field and, in some instances where the apex was obscured by vegetation, a side view photograph of the stem apex was acquired. The stem and/or branch were evaluated to determine the best lens to use in order to record all the vegetative details. Optionally, multiple images or photographs of different magnifications may be taken for each view of a plant species.

Photographs of the plants may be obtained with a standard or digital camera. Typically, the camera may be equipped with a 55-mm micro lens, or that same lens mounted in a standard fashion to 35-mm bellows. Various different lens may be used to obtain photographs. Occasionally, a 200-mm micro lens was used to record an inaccessible primary stem or branch.

Photographic images of different plant species may also be taken in a studio. In the studio, either a whole plant or a branch cutting was obtained and placed on an adjustable table. The table was positioned under various sources of light, such as but not limited to, natural light under either a skylight or where appropriate, outdoors. Various lighting methods are effective for photographing various plant structures as is known in the art photography of still subjects. The effects is typically previewed in order to select the best lighting technique for the subject. The light source(s) may be placed at various angles from the plant to optimize contrast and resolution of the structural features of the plant.

Whether the photographic images were obtained in the field or in the studio, the procedures are similar. First, a camera on a tripod was set up in a manner such that the lens was close to the plant structure, such as within a few inches of a branch apex or a stem apex. A light meter reading was taken. Optionally, color meters and color filters may be used to obtain the images. Appropriate light filters were attached to the lens as needed. Adjustments were made to bring the plant structure, such as but not limited to, the apex into focus in the viewfinder. The view was assessed to determine if all the key vegetative details were in focus, and adjustments were made as needed. Adjustments may include expanding or contracting the bellows, or removing them. The depth of field of the image was evaluated and adjusted.

In some instances, specific structural details of the plant structure to be obtained may be isolated from adjacent features by shortening the depth of field. In other instances, vegetative data could be recorded by using the greatest possible depth of field. After all adjustments were made, the photograph was taken using various sources of films or recording medium such as but not limited to, electronic/digital media, color, black and white print or slides. Under certain applications where it is more convenient to store images of prints or slides in digital format, the prints may be scanned and saved in digital format.

A variety of methods and procedures for capturing and storing images, such as but not limited to, images of plant structures, in electronic or digital format are well known in the art. In certain applications, a commercially available still digital camera may be used, and a digital memory storage unit may be used to capture and store digital data, images and photos. The data stored may be readily transferred to a computer for further data processing and manipulation.

Color, black and white prints or slides may be used to capture images of the plant species. Preferably, color images such as but not limited to, slides or prints may be taken of the plant species. Typically, 35-mm slide film may be employed. In many applications, standard commercially available films that provide high picture resolution may be used. In some applications, for example, Kodak E100S film was used.

In some applications, multiple cameras are mounted in the studio to project at different angles to the plant specimen to obtain multiple images of profiles and views at the same time without the need to adjust and move a single camera to obtain different views of the same plant species. For example, a first camera may be set up over head to obtain images of the apical complex of the plant while a second camera may be directed perpendicular to the view of the first camera such that the view of the stem or a branch of the plant species may be obtained. This method for simultaneously obtaining multiple views of a plant species allows a facile and efficient compilation of a large number of plant specimens without the need for rearranging a single camera to capture multiple views.

Different information associated with particular characteristics of each plant correlating to the images taken of the plant may be recorded in a searchable database record. For example, dated and numbered field information may be recorded for each image of the plant species taken. The characteristic information relating to the plant specimen may include: the date and time of year that the specimen was taken, the date the specimen was photographed; the plant genus, species and common name (if known), the physical location where the plant was obtained from, including the city, state and country, the owner of the plant, the planting bed and/or greenhouse location, the profiles, light sources, magnification, specimen scale (size, height), and the film roll number or slide number. The information corresponding to the unique identity of the plant specimen is stored in a particular field associated with the specimen and the data is stored in a database. The database may be stored in an electronic format that is readily amended, supplemented, and searchable.

Detailed measurements of the plant may be optionally recorded, including for example the size of the plants. Where exposed film format was employed, the film was developed into slides or prints. The slides or prints may be further stored in digital format.

The slides, prints or electronic images were organized for ease of search and retrieval. For example, the slides were organized in numerical or alphanumerical order and placed in binders in archival slide jackets. The numbers imprinted on the slides were compared to those in field notes; adjustments or correlation of the slides with the field notes were made as needed. Where feasible, the slides were compared to other slides taken of the species. Optionally, a selection of slides containing specific plant structures was chosen for enlargement. Where no digital images were previously obtained, the sorted slides were scanned using a high resolution scanner and the data stored in digital format.

The black border around each scanned slide image was cropped from the image. The image was identified with a unique identification code and stored electronically. Optionally, the information may be printed for further review or for storage and retrieval. The print was labeled with the specific roll number and slide or print number, and when known, the name of the plant's genus and species, inserted in a plastic sleeve, and organized alphabetically. When a sufficient number of images were collected from a variety of sources, comparisons may be made.

The general guides, which govern the plant kingdom, dictate the production of a specific set of features on each plant that is a member of a particular species. By comparing images from differing sources and growing conditions, a set of species-specific characteristics could be determined and the photographic methodologies refined. Different sources and conditions in which the plants are obtained is of significance because plants survive in a broad range of growing conditions, and the extreme conditions will frequently expose the minimum set of characteristics of the plant that the plant will retain. For example, under more favorable growing conditions for a particular plant, the plant will exhibit certain characteristics that are not observed under different conditions. For example, the spine shield of a species may not be as dried or atrophied in favorable growing conditions in a particular environment. Therefore, a minimum set of characteristics will be revealed and captured when a comparison is made of images from different plant specimen, sources, and growing conditions. These methodologies may be adjusted and updated as needed in order to capture the salient characteristics of different species obtained under different conditions.

Identification of Unknown Plant Specimens:

Sample Database and Method for Identifying Unidentified Plants:

The following is an example of a process for the identification of an unknown or unidentified plant species using a database. In this particular example, the sample database was compiled for the identification of a specific species of plant, such as but not limited to, a succulent rosette.

The database leads from cultivated plants with rosette-form vegetation to succulent rosette species with spiral leaf formation. The database incorporates apical complex photographs. Every section may be supplemented with visual guides, such as but not limited to, photographs, pictures or drawings. In addition, in each step or section, there is provided text to guide the user to identify the unknown or unidentified plant.

Figure 2A:
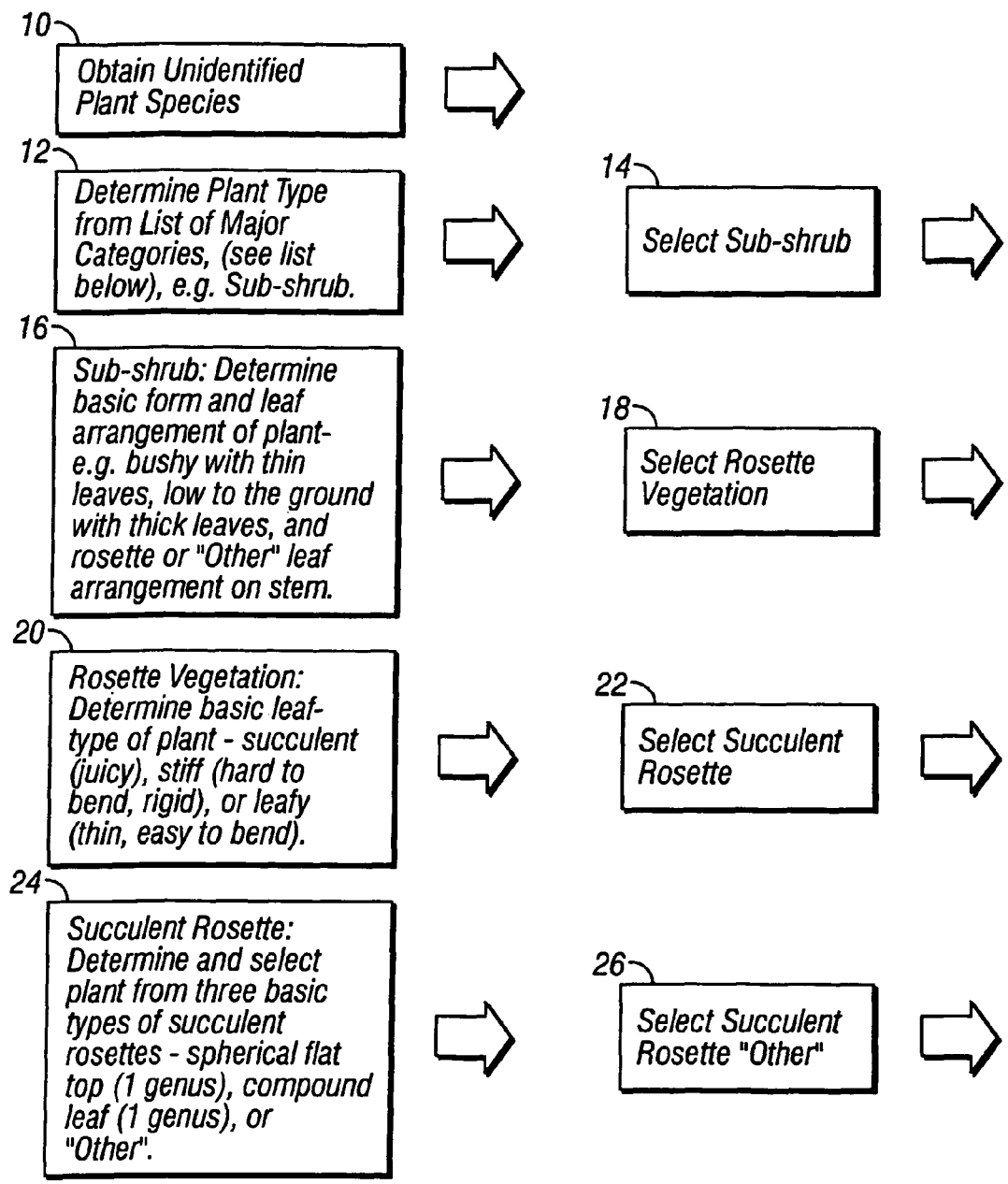
FIGS. 2A and 2B show a flow chart of one example of a method of identifying unknown plant.
Figure 2B:
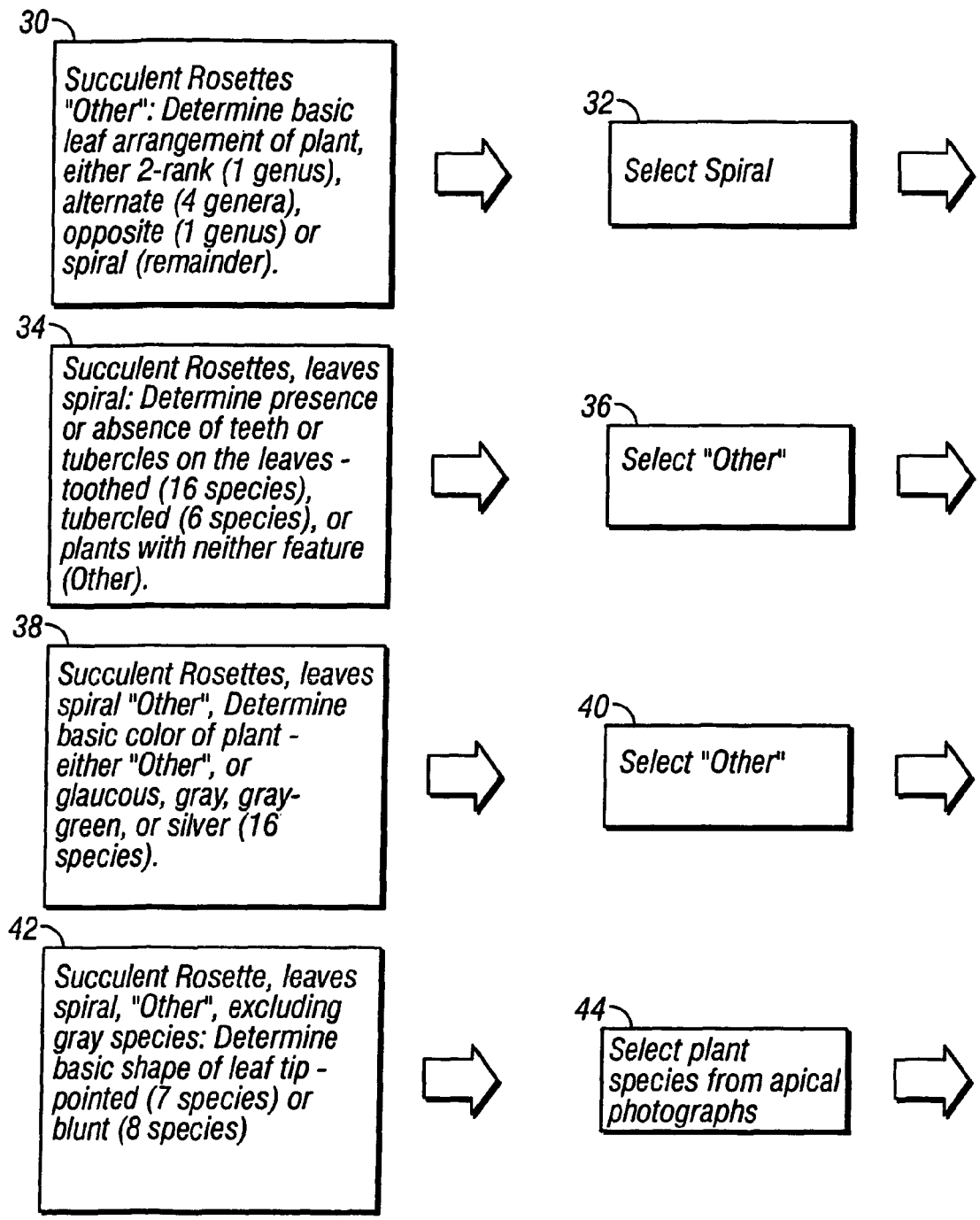

Referring now to FIGS. 1 and 2, a block diagram illustrating a method for identifying unidentified or unknown plant species will now be described. By way of example and not limitation, FIGS. 1 and 2 show one method a user may use to identify an unknown succulent rosette subshrub plant, concentrating and selecting from those plants useful to collectors worldwide. Succulent plants are widely collected internationally. The market for this product will be readily accessible through existing societies interested in succulents and through specialized growers.

FIG. 1 at block 10 shows that the user obtains an unidentified plant species which at block 12, the user determines which major plant type the plant belongs to. As will be described in FIG. 7, embodiments of the present invention will provide visual images and text prompts that will guide the user through the identification steps recited herein. In this example, the user selects Sub-schrub as indicated by block 14. From the sub-schrub selection, the user determines what type of basic form and leaf arrangement the plant has, as indicated at block 16. The user selects, for this example, rosette vegetation (block 18). Under rosette vegetation at block 20, the user determines the basic leaf type. In this example, user selects the succulent rosette at block 22. The user then determines where the unidentified plant fits in the three basic types of succulent rosettes (block 24). The user selects succulent rosette category "other" as indicated at block 26.

FIG. 2 continues the description of the process begun in FIG. 1. Block 30 shows that under succulent rosette category Other, the user selects the basic leaf arrangement of the plant. Block 32 indicates that the user selects spiral. Block 34 shows that the user then determines the presence of teeth or tubercles on the spiral leaves. Plant with neither may be selected with the Other option, which the user selects in block 36. The user then determines the color of the plant at block 38. Again, if the plant does not match the options presented, the user may again select the Other option (block 40). The user at block 42 may then determine basic shape of the leaf tip. Block 44 then presents the available species (7 species for tip pointed or 8 for blunt tipped).

The following are the major categories of types of plants:

| | | |
|---|---|---|
| 1. Aquatic | A plant that requires excessive moisture in order to thrive. The ground or pot in which they grow is very wet, soggy, or pooling. | |
| 2. Vine | A plant with slender stems (woody or soft) that grows along the ground or climbs on another plant. Many will support themselves by winding around another plant or structure and grasp with either tendrils or fibrous root-like growths that grasp the support. | |
| 3. Ferns | A non-flowering evergreen or deciduous plant often with feather-like fronds (leaf-like vegetation) generally growing from a central point. Most | |

|   |   |
|---|---|
|   | ferns have fronds emerging from a central point at ground level, some form a trunk, appearing much like a small feathery palm tree. |
| 4. Insectivores | A plant adapted to feeding on insects by trapping them with fly trap (hinged), pitcher-shaped, or sticky tentacular leaves. |
| 5. Orchids | A huge family of plants cultivated for and recognized by, its complex, showy, long-lived flowers. When not in flower, some of them can be recognized by their sympodial or monopodial growth habits, a fairly simple leaf structure, and the presence of aerial or exposed roots. The most common species are sympodial in which new growth emerges from a ground level horizontal rhizome first creating a pseudobulb with persistent leaves emerging from the top of the pseudobulb. These species usually have conduplicate leaves which are smooth, thick, entire, leathery, lance-shaped green leaves with a center fold and parallel veins. Others have plicate leaves - multi-folded, like a fan. In monopodial species, the leaves emerging from the top of the previous years growth. These species usually have simple leaves as well (non-fan-shaped). |
| 6. Cactus | Typically a succulent, leafless, spiny plant with a thick, fleshy stem. Some have a branching pattern, others form a single column, a single globe, or a cluster of globes. Most have spines and a distinct growing point called an "areole" spread over the surface of the stem, from which the spines emerge. The most familiar are the large Saguaro columnar species typical of the American southwest, or Opuntias, a group recognized by their "pads" and shrubby branching habit. Most grow in hot, arid regions of the Americas. |
| 7. Grass | A large group of plants with round, usually hollow stems frequently distinguished by their regularly spaced nodes or joints. These plants are also characterized by their sheathing leaves that wrap around the stalk. Many are grown and used for grazing. Bamboo and hay are both grasses. |
| 8. Sub-shrubs | A small perennial shrub, typically with soft pliable leaves (herbaceous) or soft-wooded. Some grow under the shadow of larger plants, others in full sun. |
| 9. Shrubs | A woody plant lacking a trunk with multiple stems emanating from the base. Some are quite large. Most are smaller than a tree. |
| 10. Palms | Most are medium-sized to tall unbranched trees with a crown of large distinct "palm" leaves (large pinnate or palmately cleft leaves). Most are unbranched and have leaves clustered at the top of the trunk. Many have a bare, smooth-barked trunk, others have a coarse trunk comprised of the persistent base of old fronds. |
| 11. Tree | A large woody perennial plant usually with a single self-supporting stem or trunk. The top is usually covered with numerous spreading branches. Some have persistent leaves, some loose a few leaves on a regular basis, others are deciduous and loose their leaves each year. |

The sample database incorporates apical complex photographs and various unique physical characteristic of a variety of plants, including the apical complex. In this particular example, the specific characteristics include the physical characteristics of a succulent species. In the identification process, every page (or screen page) or identification prompt, such as but not limited to, text with photographs, may be supplemented with visual guides, such as but not limited to, photographs, figures or drawings, or audio guides, or various combination therein. An example of such a process using text as a guide for the identification of a plant, is provided herein.

| Page I List of Plant Types |   |
|---|---|
| 1. Aquatic |   |
| 2. Vines |   |
| 3. Ferns |   |
| 4. Bamboo |   |
| 5. Insectivores |   |
| 6. Orchids |   |
| 7. Cactus |   |
| 8. Sub-shrubs | ⇒ |
| 9. Shrubs |   |
| 10. Palms |   |
| 11. Trees |   |
| Page II Sub-shrubs | |
| 1. Rosette vegetation⇒ |   |
| 2. Other |   |
| Page III Rosette (114 Genera) | |
| 1. Succulent rosettes | ⇒ |
| 2. Stiff rosettes | (29 genera - e.g. *Bromeliads*, *Yuccas*) |
| 3. Leafy rosette | (50 genera) |
| Page IV Succulent rosettes | |
| 1. Spherical flat top = | *Ariocarpus* (6 species) Apical photographs will come up on next page. END |
| 2. Leaf compound = | *Morisia* (1 species) Apical photographs will come up on next page. END |
| 3. Other = | 14 genera⇒ |
| Page V Succulent rosettes Other | |
| 1. 2 ranked leaves = | *Gasteria* |
| 2. Leaves alternate = | *Aichryson*, *Echeveria*, x*Pachyveria*, *Sedums* |
| 3. Leaves opposite = | *Sedums* |
| 4. Leaves spiral | ⇒ |
| Page VI Succulent rosettes, leaves spiral | |
| 1. Leaf margins toothed = | 16 species (*Aloes*, *Haworthia*, *Aeonium*). Apical photographs will come up on next page. END |
| 2. Leaf has tubercles = | 6 species (*Haworthias*). Apical photographs will come up on next page. END |
| 3. Other | ⇒ |
| Page VII Succulent rosettes, leaves spiral, Other | |
| 1. Glaucous, gray, gray-green, & silver = | 16 species. Apical photographs will come up on next page. END |
| 2. Other | ⇒ |

| Page VIII Succulent rosettes, leaves spiral, Other, excluding gray species | |
| --- | --- |
| 1. Pointed leaf tip = | 7 species. Apical photographs will come up on next page. END |
| 2. Rounded, blunt leaf tip = | 8 species. Apical photographs will come up on next page. END |

Vertical Parameters used for this sort was derived from The American Horticultural Society *Encyclopedia of Garden Plants*: A to Z Encyclopedia. This includes 2100 genera and 15,000 species; 114 genera have rosette-form vegetation.

Examples of horizontal Parameters used for this sort:
1. banded sometimes
2. basal
3. blotched
4. bluish green gray
5. center lvs closed
6. center lvs point upward, others flatten
7. chalky
8. ciliate
9. climbing
10. clump
11. cobwebs
12. compressed center, loose perimeter
13. conical
14. cushion
15. dark green
16. filamentose
17. fimbriate
18. glaucous
19. glossy
20. grasslike
21. gray-green
22. hairy
23. incurved
24. irregular cross-bands
25. lavender
26. leafy
27. lf 'v' shaped
28. lf arches
29. lf club
30. lf cylinder
31. lf dotted, spots
32. lf inverse lance
33. lf lance
34. lf linear
35. lf long flat narrow
36. lf narrow oblong
37. lf needle
38. lf oblong
39. lf oblong-obovate
40. lf oblong-triangular
41. lf obovate
42. lf obovoid
43. lf oval
44. lf ovate
45. lf round
46. lf spoon
47. lf sword
48. lf tapering
49. lf triangle
50. lf wedge-shape
51. light green
52. lvs fuzzy
53. lvs overlap
54. lvs point upward
55. lvs pressed together
56. lvs spaced
57. lvs thick
58. margin angular
59. margin blunt
60. margin contrasting color
61. margin fringed wavy
62. margin horny
63. margin incurved
64. margin rounded
65. margin spiny
66. margin spots on
67. margin striped
68. margin toothed
69. margin winged
70. mat
71. mid green
72. moist
73. olive green
74. overall bowl shape
75. overall cup shape
76. overall flat saucer shape
77. pale green
78. purple
79. recurved
80. reddish
81. ridge on outside of lf
82. rough
83. semi-open fist, loose sphere
84. silver gray
85. slightly grooved, rough
86. smooth
87. sphere, all lvs closed fist
88. stem forms
89. succulent
90. tessellate
91. tip blunt
92. tip blushed
93. tip bristle brown
94. tip contrast
95. tip hairy
96. tip minute papillae
97. tip pointed
98. tip round
99. top slightly flat
100. transparent contrast marks
101. tubercles
102. tuft
103. variegate
104. wart
105. waxy granules
106. woolly In the above example, a user having an unidentified plant is prompted through the identification process by reviewing, comparing and answering a set of queries designed to lead the user through the process for identifying the unidentified plant.

In other applications as disclosed herein, particular feature(s) or characteristic(s) of an unidentified plant is scanned into a computer system and the computer searches, compare and automatically identifies the unidentified plant using a stored database. In one variation, the user may be able to identify the plant using a combination of an automatic computer search with a (manual) step through prompt and query procedure that is elicited from the computer.

Figure 3:
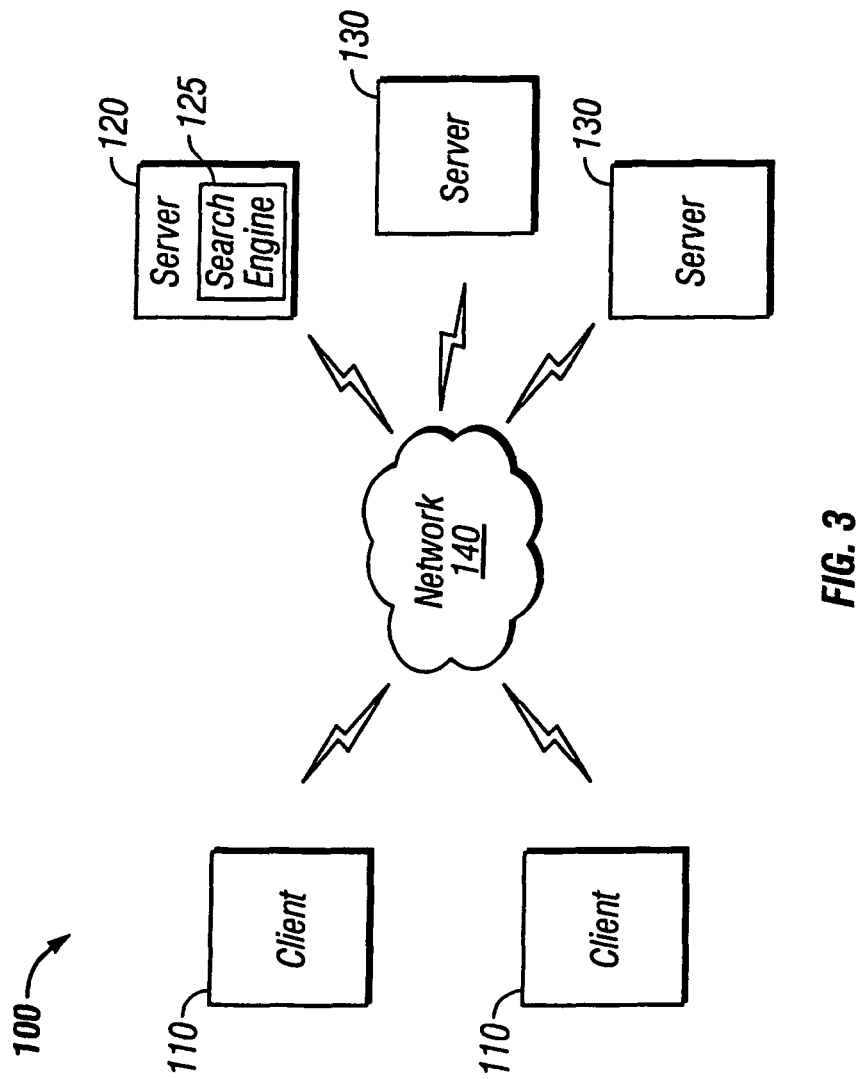
FIGS. 3 and 4 shows the overview of one embodiment of a computer network and computer for use with the present invention.

FIG. 3 illustrates a system 100 in which methods and apparatus, consistent with the present invention, may be implemented. The system 100 may include multiple client devices 110 connected to multiple servers 120 and 130 via a network 140. The network 140 may include a local area network (LAN), a wide area network (WAN), a telephone network, such as but not limited to the Public Switched Telephone Network (PSTN), an intranet, the Internet, or a combination of networks. Two client devices 110 and three servers 120 and 130 have been illustrated as connected to network 140 for simplicity. In practice, there may be more or less client devices and servers. Also, in some instances, a client device may perform the functions of a server and a server may perform the functions of a client device.

The client devices 110 may include devices, such mainframes, minicomputers, personal computers, laptops, personal digital assistants, or the like, capable of connecting to the network 140. The client devices 110 may transmit data over the network 140 or receive data from the network 140 via a wired, wireless, or optical connection. By way of example and not limitation, client devices may be connected to the network 140 via dial-up, ISDN, DSL, cable, satellite modems or the like, via wireless network interface hardware, or the like. In one configuration, the plant image database is stored on a server 130 and the users on client devices 110 may access the database through a web interface or via a client running on the client device 110.

Computer network 140 is typically a wide area network (WAN) such as but not limited to, the Internet, or the like. In this embodiment, computer network 140 may use communication protocols such as but not limited to, TCP/IP, RTP, RTSP, or the like for the transfer of data. In other embodiments, computer network 140 may be a local area network (LAN), based upon TCP/IP, IPX, or the like. Data communication may include transfer of HTML based data, textual data, form submissions, plug-in programs or viewers, applets, packetized audio or video data, real-time streaming data, and the like. Although computer network 140 is illustrated as a single entity, as is the case with the Internet, it should be understood that computer network 140 may actually be a network of individual computers and servers. The database of plant images and text keys may be stored in a distributed manner over a plurality of servers or alternatively, all on one server.

Figure 4:
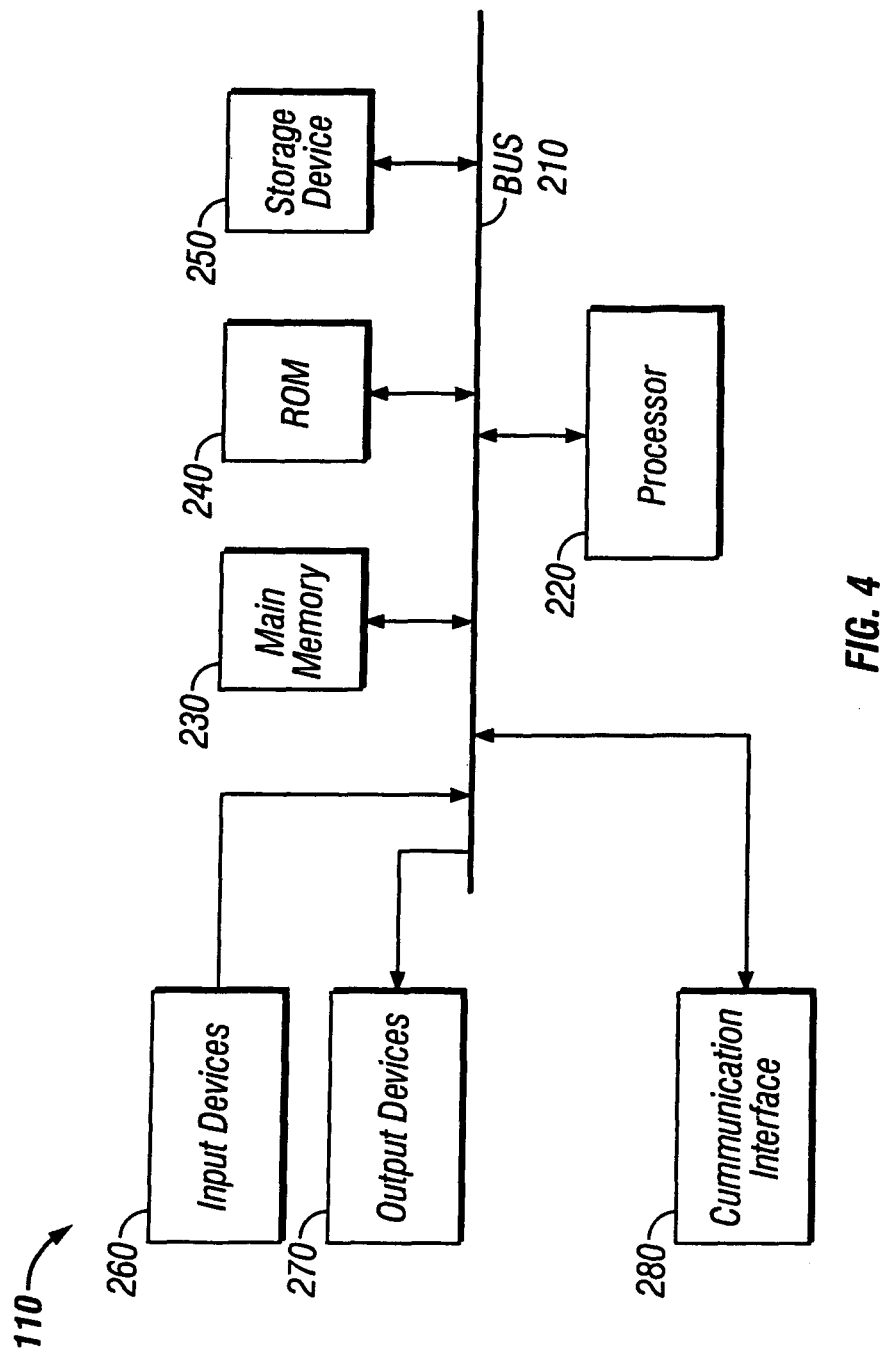

FIG. 4 illustrates one embodiment of a client device 110 consistent with the present invention. The client device 110 may include a bus 210, a processor 220, a main memory 230, a read only memory (ROM) 240, a storage device 250, an input device 260, an output device 270, and a communication interface 280.

The bus 210 may include one or more conventional buses that permit communication among the components of the client device 110. The processor 220 may include any type of conventional processor or microprocessor that interprets and executes instructions. The main memory 230 may include a random access memory (RAM) or another type of dynamic storage device that stores information and instructions for execution by the processor 220. The ROM 240 may include a conventional ROM device or another type of static storage device that stores static information and instructions for use by the processor 220. The storage device 250 may include a magnetic and/or optical recording medium and its corresponding drive. Images of plants species may be stored at the server 130. The user may optionally download searches and plant species images to the local computers or client device 110.

The input device 260 may include one or more conventional mechanisms that permit a user to input information to the client device 110, such as but not limited to, a keyboard, a mouse, a pen, voice recognition and/or biometric mechanisms, etc. The output device 270 may include one or more conventional mechanisms that output information to the user, including a display, a printer, a speaker, etc. The communication interface 280 may include any transceiver-like mechanism that enables the client device 110 to communicate with other devices and/or systems. For example, the communication interface 280 may include mechanisms for communicating with another device or system via a network, such as network 140.

In one embodiment, client device 110 is a PC compatible computer having an X86 based microprocessor, an ATHLON™ microprocessor from Advanced Micro Devices, Inc., or the like. Further, in the present embodiment, client device 110 typically includes a Windows WINDOWS® operating system such as but not limited to, WINDOWSME®, WINDOWSNT®, WINDOWS XP®, or the like from Microsoft Corporation.

RAM and disk drives are examples of tangible media for storage of data, audio/video files, computer programs, browser software, embodiments of the herein described invention, applet interpreters or compliers, virtual machines, web pages, databases such as but not limited to, ORACLE® 8i from Oracle Corporation, and the like. Other types of tangible media include floppy disks, removable hard disks, optical storage media such as but not limited to, CD-ROMS and bar codes, semiconductor memories such as but not limited to, flash memories, read-only-memories (ROMS), battery-backed volatile memories, and the like. In embodiments of the present invention, such as but not limited to, set top boxes, mass storage, such as but not limited to, disk drive, and the like may be dispensed with.

In the present embodiment, client device 110 may also include software that enables communications over a network such as but not limited to, the HTTP, TCP/IP, RTP/RTSP protocols, and the like. In alternative embodiments of the present invention, other communications software and transfer protocols may also be used, for example IPX, UDP or the like.

FIG. 4 is representative of types of computer systems for embodying the present invention. It will be readily apparent to one of ordinary skill in the art that many other hardware and software configurations are suitable for use with the present invention.

For example, other types of processors are contemplated, such as but not limited to, PENTIUM®, CELERON®, or other microprocessors from Intel Corporation; POWERPC® G3, G4 microprocessors from Motorola, Inc.; CRUSOE® microprocessors from Transmeta, and the like. Further other types of operating systems are contemplated, such as but not limited to, SOLARIS® from Sun Microsystems, Inc.; LINUX; UNIX® (trademark owned by X/Open Company, Ltd.); MAC OS® from Apple Computer Corporation and the like. In still other embodiments, set top boxes such as but not limited to, the PS2 (PLAYSTATION®2) from Sony Corporation, XBOX® and WEBTV® from Microsoft Corporation and the like may also be used.

As will be described in detail below, the client devices 110, consistent with the present invention, perform certain searching-related operations. The client devices 110 may perform these operations in response to processor 220 executing software instructions contained in a computer-readable medium, such as but not limited to, memory 230. A computer-readable medium may be defined as one or more memory devices and/or carrier waves. The software instructions may be read into memory 230 from another computer-readable medium, such as but not limited to, the data storage device 250, or from another device via the communication interface 280. The software instructions contained in memory 230 causes processor 220 to perform search-related activities described below. Alternatively, hardwired circuitry may be used in place of or in combination with software instructions to implement processes consistent with the present invention. Thus, the present invention is not limited to any specific combination of hardware circuitry and software.

The servers 120 and 130 may include one or more types of computer systems, such as but not limited to, a mainframe, minicomputer, or personal computer, capable of connecting to the network 140 to enable servers 120 and 130 to communicate with the client devices 110. In alternative implementations, the servers 120 and 130 may include mechanisms for directly connecting to one or more client devices 110. The servers 120 and 130 may transmit data over network 140 or receive data from the network 140 via a wired, wireless, or optical connection.

The servers may be configured in a manner similar to that described above in reference to FIG. 4 for client device 110. In an implementation consistent with the present invention, the server 120 may include a search engine 125 usable by the client devices 110. The servers 130 may store documents (or web pages) accessible by the client devices 110.

Secure connections from the client to the server may be implemented. In such an embodiment, communication between these servers may be via a virtual private network (VPN), or other secure protocol, such as but not limited to, an SSL or HTTP.

By way of example and not limitation, the application of the present invention for plant identification may be implemented within a framework of an Application Service Provider (ASP) system embedded in a central service computer platform 130 having a network interface. Server platform 130 can be a single workstation such as a PC, a mainframe computer or a collection of computers interconnected by a local or wide area network. Server platform 130 is capable of handling web-enabled technologies by means of web server applications such as BEA WEBLOGIC® Server from Oracle Corporation which supports Hypertext Transfer Protocol (HTTP). Such technologies include for example JAVA® applets, JAVASCRIPTS®, HTML, DHTML, XML, and the like on the client side, and Servlets, Java Pages (JSP) and Enterprise Java Beans (EJB) and the like on the server side. A user of the system communicatively interfaces over a data communication network, such as the Internet or Intranet, to central server 130 by conventional communication devices such as a modem, a network card and the like, using a software application, i.e., Web Browsing (e.g., INTERNET EXPLORER® from Microsoft Corporation and NAVIGATOR™ from Netscape Communications Corporation. User may access server 130 via other software application such as a client software application on client 110 specifically designed to interact with the server 130. By way of example but not limitation, Web Browser is shown as the preferred embodiment in this document. Through the browser (in association with a display device and input devices such as a keyboard and mouse), a user can upload data into server 130 and can request and receive dynamic on-line information and services from the different server modules. For example and not limitation, the user may access the plant identification system. The system may also be configured to allow users to submit new plant species to the plant database (which may be pending approval by system administrator). It will be readily appreciated that server 130 may be located on a local area network within the organization of the user. Similarly it will be readily appreciated that a user may access server 130 not directly from user system but from other "on the road" computing devices such as Laptops, Personal Data Assistance units and the like. The person skilled in the art will appreciate that other methods of data input and transmission between the user and server 130 are contemplated by the present invention. In yet another embodiment of the present invention the server 130 may reside within a user system or within an Intranet or local area network relating to user for local or single use by a user or a group of users. Alternatively the various components of the system may reside on various computers not limited in location or networks and connected there between via known data communication device creating a distributed network of computers providing the same functionality as shown in this invention.

Figure 5:
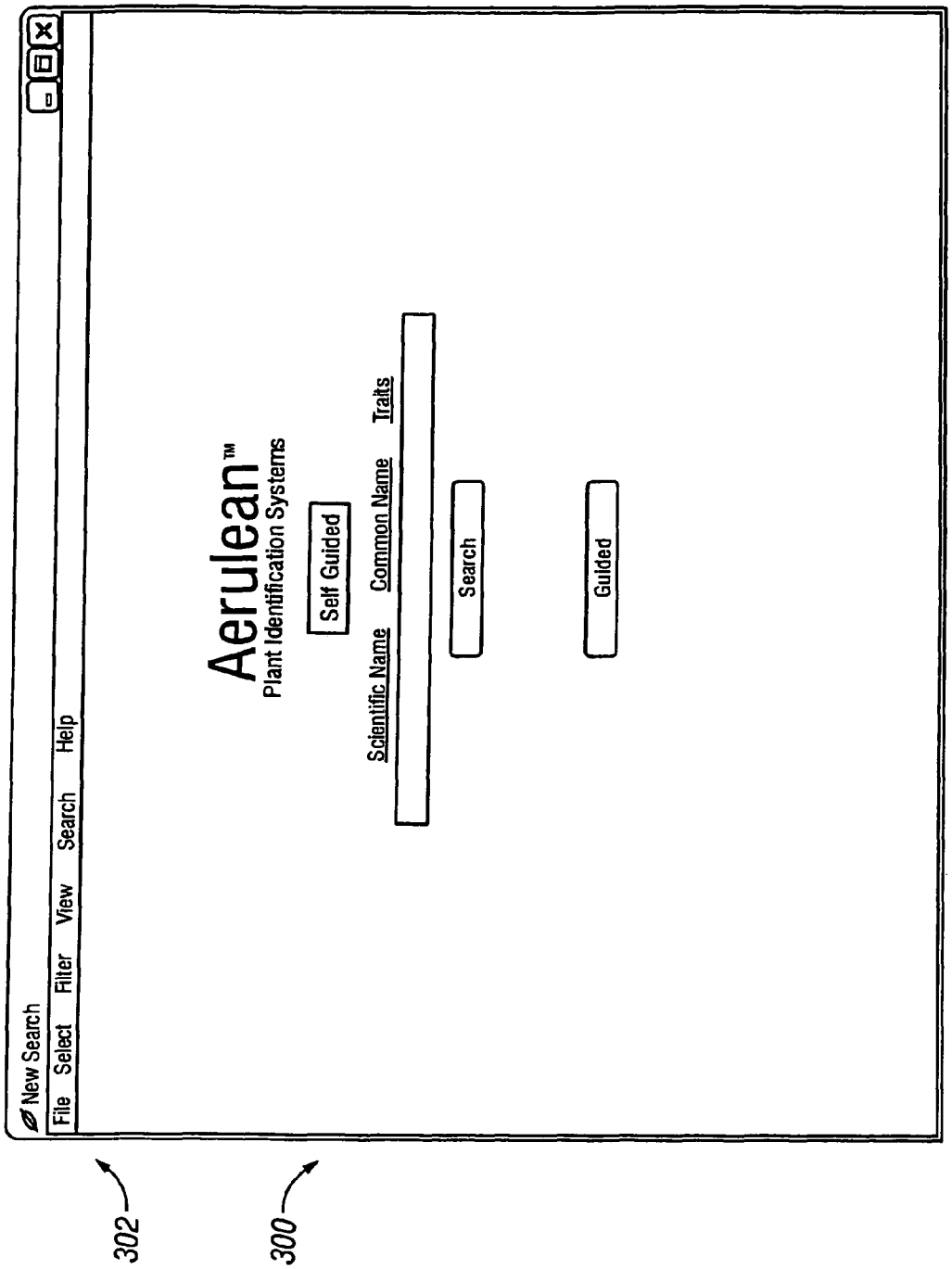
FIGS. 5 through 11 show screen shots of user interfaces according to the present invention.

Referring now to FIG. 5, one embodiment of a computer-implemented method according to the present invention will now be described. In one embodiment, the present invention creates a web-based plant identification system using visual keys that can be easily navigated by a user interested in identifying an unknown plant. The present invention for plant identification makes it possible for professionals as well as novice users to conduct extremely efficient blind searches.

In one embodiment of the present invention, the identification system will be navigated using visual and text prompts. Each navigation thread will lead to images of specific plants. By way of example and not limitation, the basic system may include 60,000 cultivated plants. This system can be made available to users on a subscription basis and customized to meet the specific plant-management needs of major growers and others who manage large collections.

By way of example and not limitation, one example of a system according to the present invention will be a web-based identification system containing cultivated species in the Cactus Family, concentrating on those plants useful to collectors worldwide. Members of the Cactus Family are widely collected internationally. The market for this product will be readily accessible through existing societies interested in the Cactus Family and through specialized growers.

Referring now to FIG. 5, one embodiment of a user interface 300 according to the present invention is shown. This user interface 300 includes a plurality of drop down menus 302 which allow the user to, among other things, load a new or saved search. If the user has particular key words, the user may enter them in the text box 304 and perform key word searches for particular plants. By way of example and not limitation, the searches may be for scientific names, common names, and/or plant traits to name a few of the categories. Of course, other categories may also be selected. The drop down menus may also allow the user to pursue a guided search as will be discussed further below.

Figure 6:
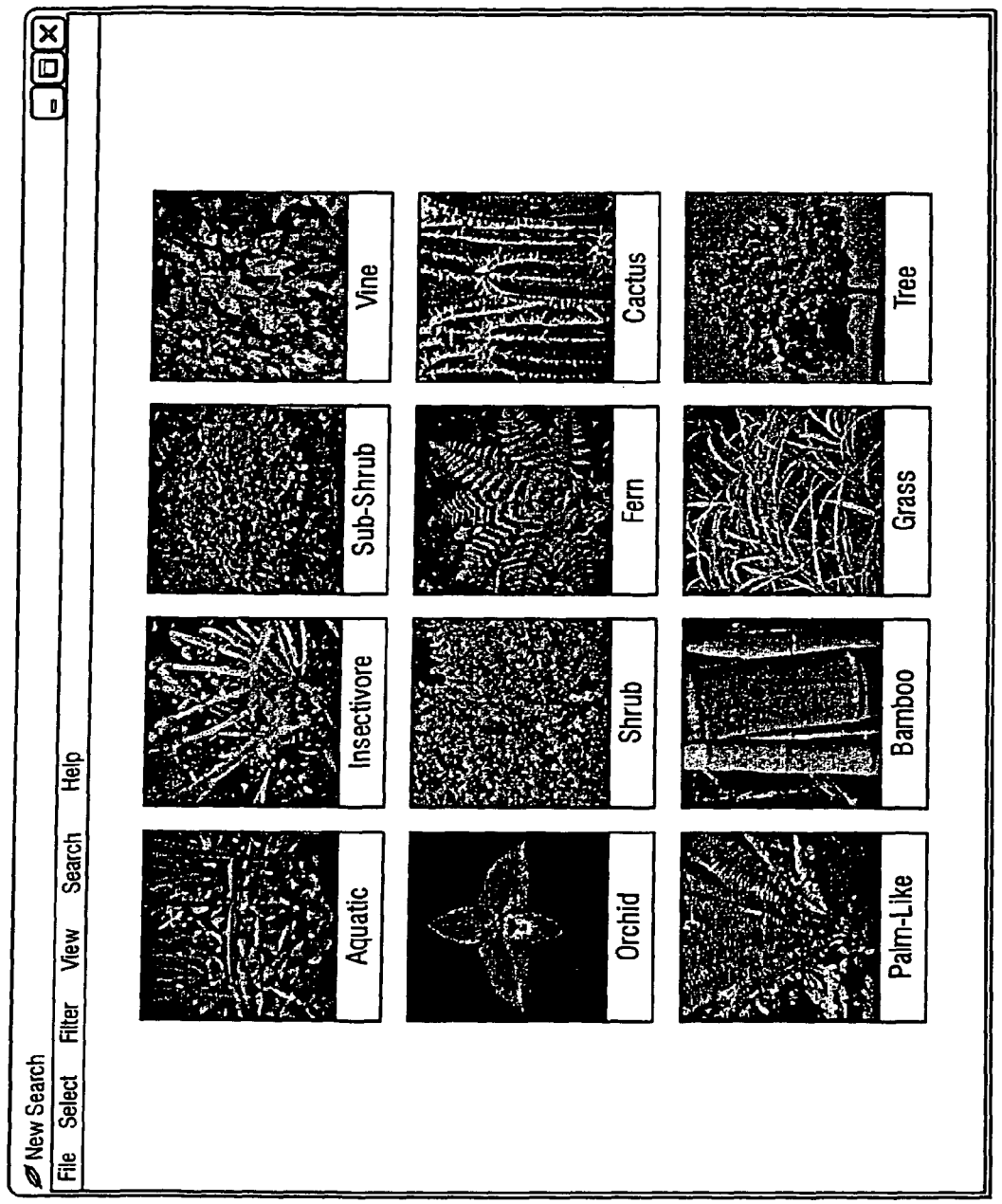

Referring now to FIG. 6, if the user has selected a guided search from the user interface presented in FIG. 5, another interface 320 will be displayed showing a variety of plant groups. By way of example and not limitation, the interface 320 may show plant groups for aquatics, insectivores, subshrubs, vines, orchids, schrubs, ferns, cacti, palms, bamboos, grasses, and/or trees. It should be understood that further plant groups may also be displayed and that these additional groups may be displayed on the same screen or linked to display on another page of the user interface. The user may move the cursor to select the desired group. The process for a guided search will also be discussed in regards to FIG. 13.

Figure 7:
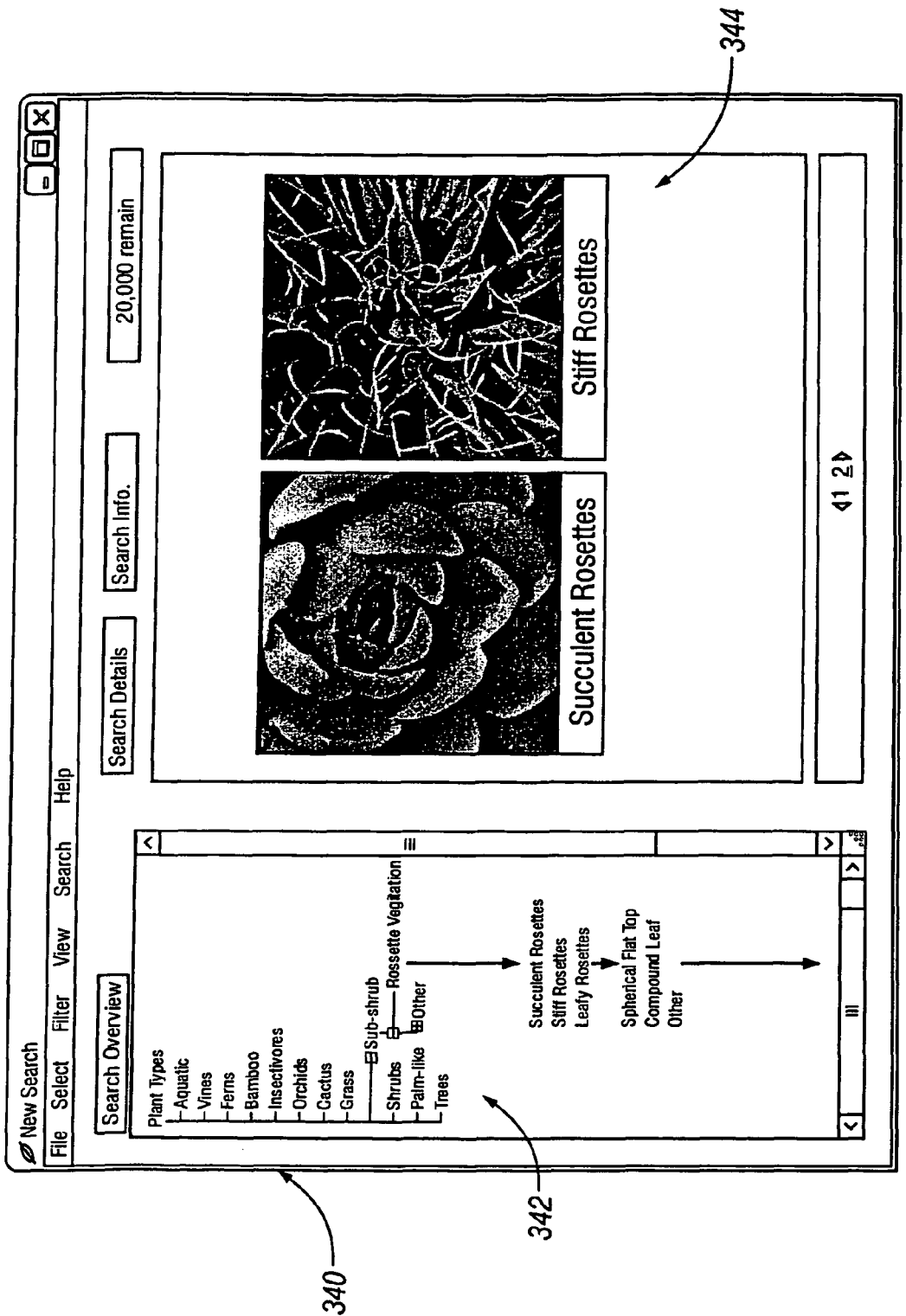

Referring now to FIG. 7, interface 340 shows how the user will be prompted by both text and images to select the traits for identifying the plant. In some embodiments, the user may skip ahead by scrolling down the text window 342. As seen in FIG. 7, the user may select from a pair of traits. The traits may be presented as both text and photos. The text is shown in window 342 and the images are shown in image window 344.

Figure 8:
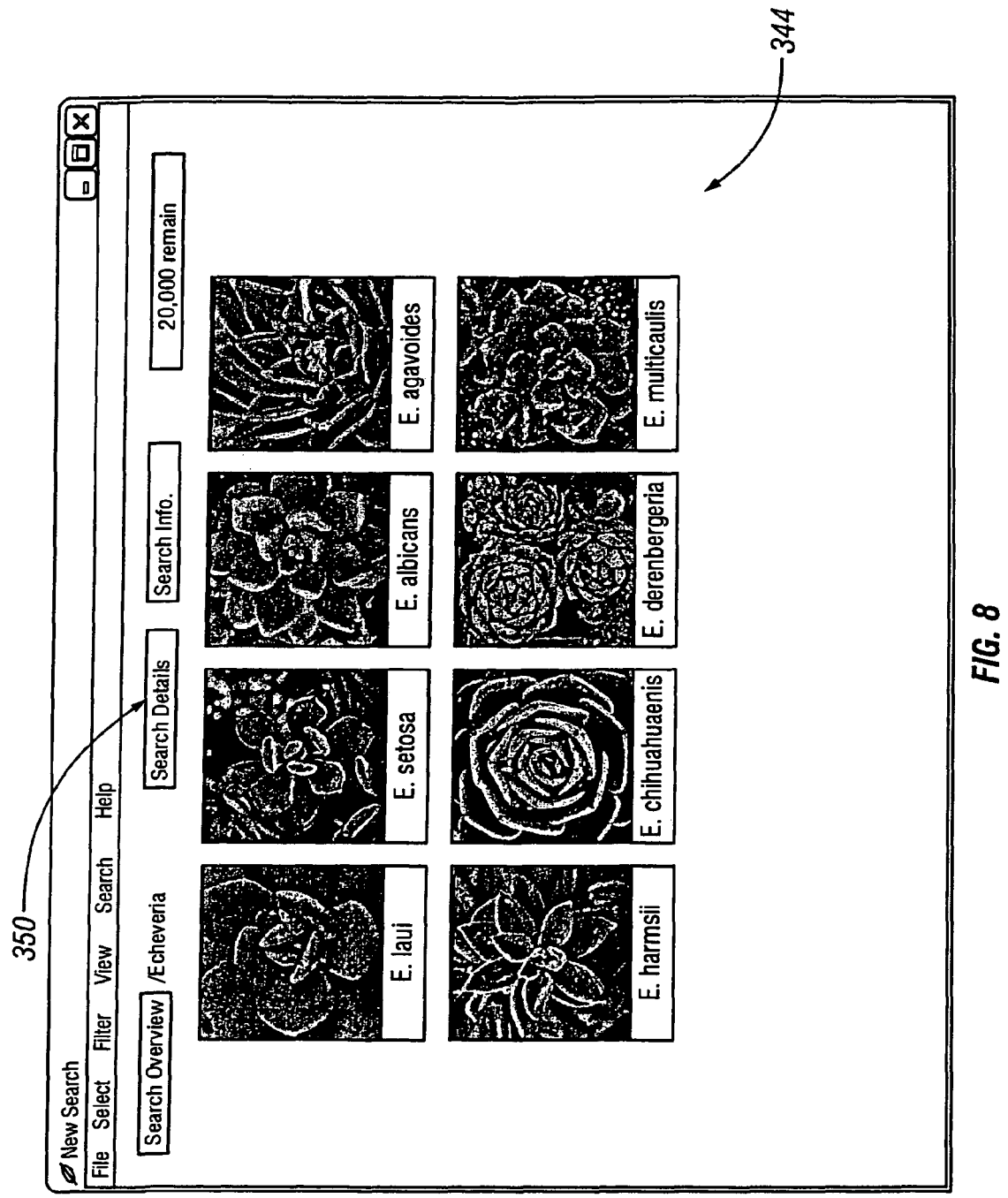

Referring now to FIG. 8, additional screen shots show that the user may be guided by images for identification of the plant. FIG. 8 also shows that tabs 350 may be included at the top of the various windows to present the user the appropriate information for each search mode. The tabs represent various modes.

Figure 9:
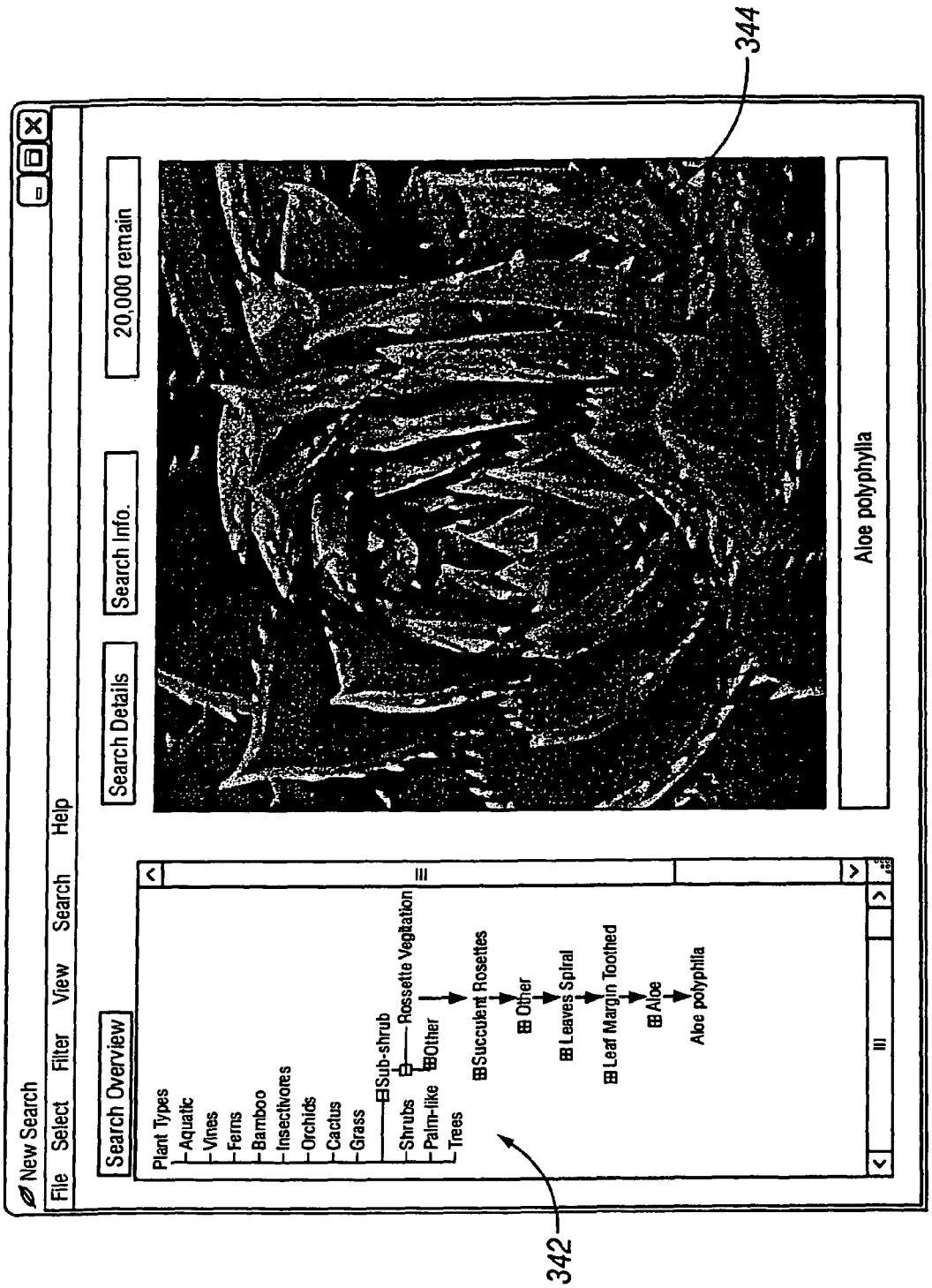

FIG. 9 shows a user interface with the text window on the left and the image window on the right. FIG. 9 shows that the user has guided down several iterations and that the image on the right shows a close up of the desired plant.

Figure 10:
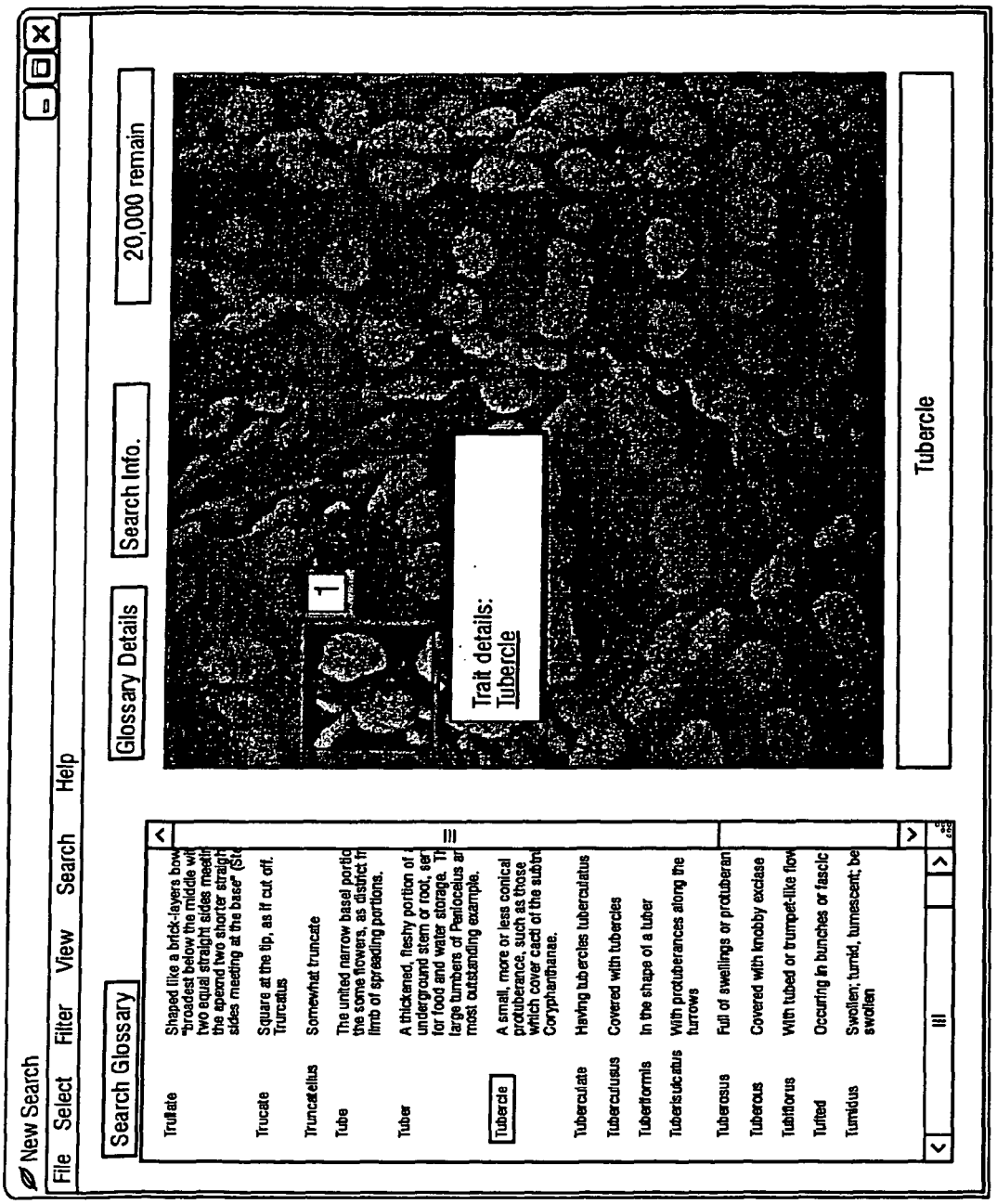

FIG. 10, a glossary screen shot, shows a trait on the profile view of a plant. This view may be accessed or activated by the user and will highlight traits that are used to identify a plant. This feature may be used to illustrate multiple glossary terms in a single photograph, or to clarify the location of a specific trait. This feature will be used primarily when the user will benefit from the enhanced isolation of a specific trait.

Figure 11:
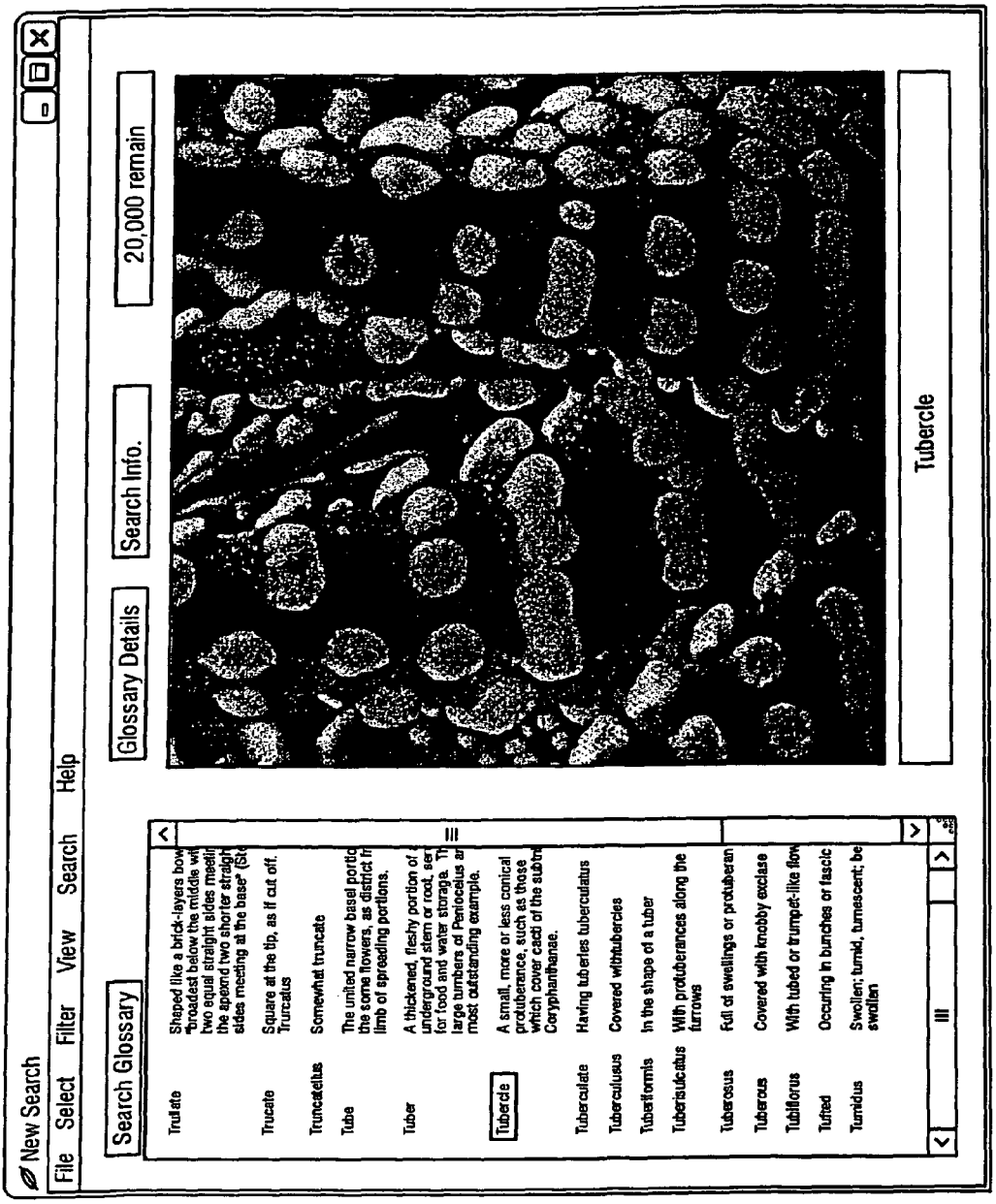

FIG. 11, a second glossary screen shot, shows another use of a glossary. The glossary mode can be accessed without losing the guided or self-guided search. Glossary terms will be illustrated to emphasize the basic character of a trait. Some glossry terms may require multiple images. This treatment will be used when the trait is extremely variable (and a single image could lead to confusion.)

Various flowcharts and schematic showing the process of searching a plant identification database will now be described in more detail.

Figure 12:
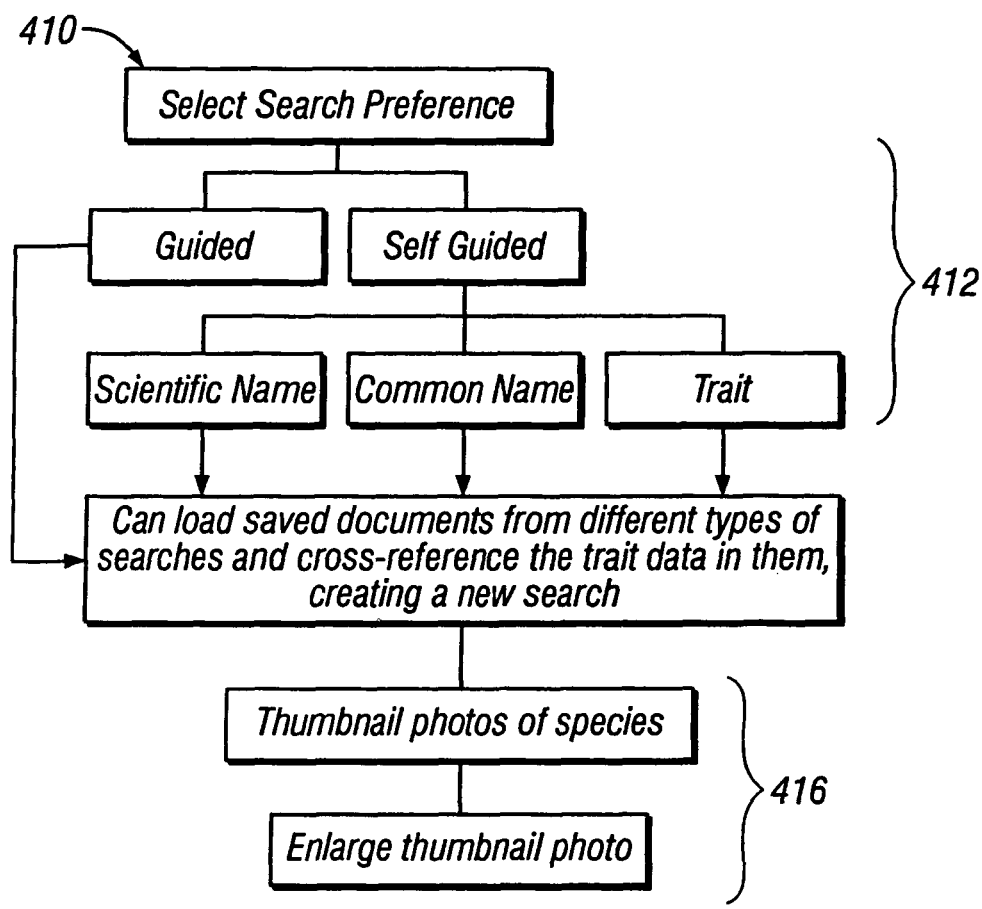
FIGS. 12 through 16 show flow charts for various embodiments of plant identification searches.

Referring now to FIG. 12, a schematic showing the process of initial search type selection will now be described. After arriving at the user interface 300 as shown in FIG. 5, the user may opt to select a search preference as shown in block 410. By way of example and not limitation, the user may select from a guided search or a self-guided search, which includes a scientific name search, a common name search, or a trait search at step 412. In a unique mode, the system may optionally allow a user to load saved documents from different types of searches, cross-reference the species data in them, and then create a new search. In this mode, the user can limit the new search to the data contained in the saved searches. From there, the user may follow the process as outlined for each particular type of search and may view photos of various plant species and enlargements of desired plant images. In one permutation, the user may load an old search, than start a new search-within-a-search using a variation of the search window shown in FIG. 5.

Figure 13:
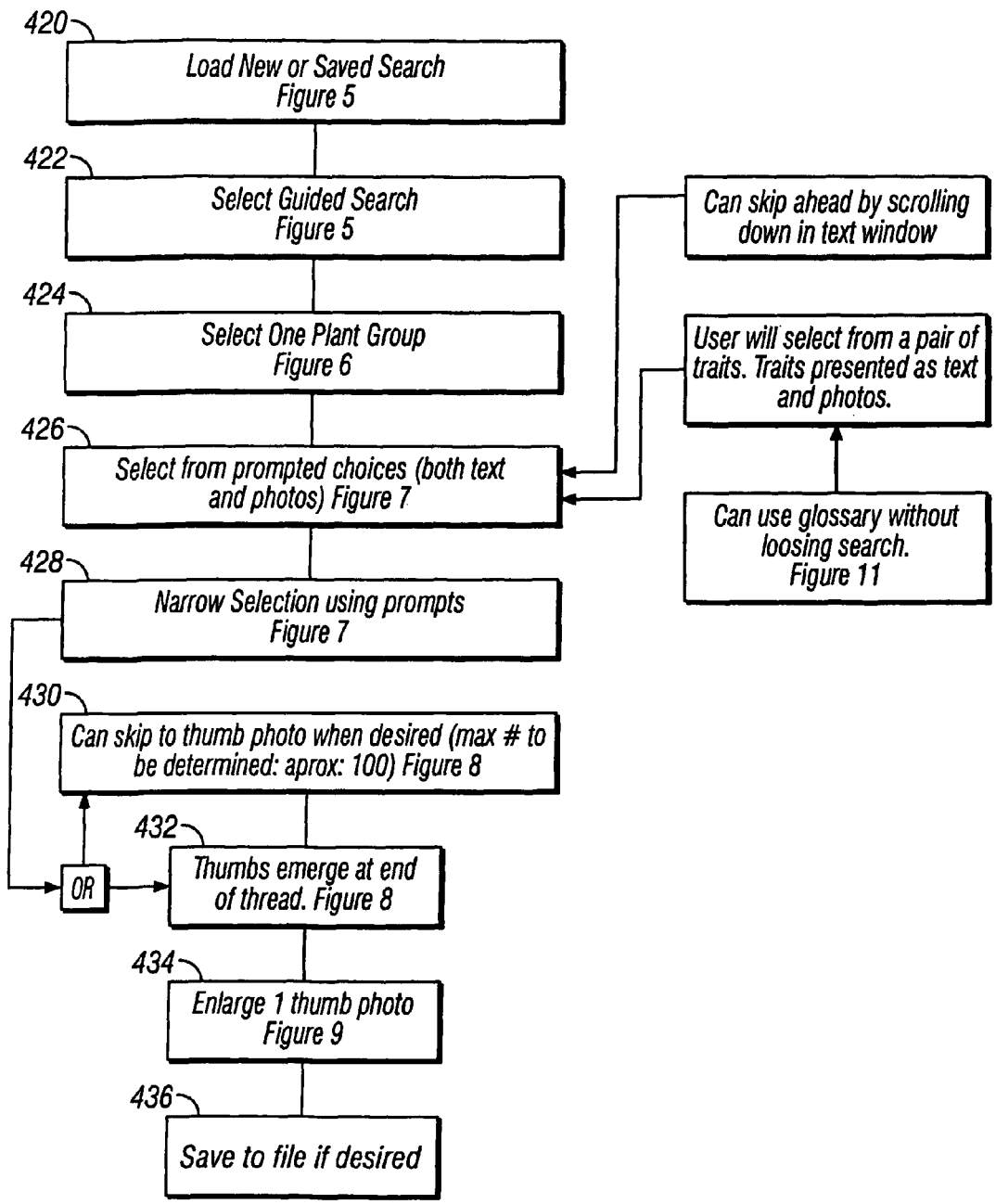

In another permutation, the user may load multiple searches to compare images. FIG. 13 shows one embodiment of the process a user may take in a guided search. As seen in FIG. 13, the user is presented with several options including opting to load a previously saved search as indicated at block 420. This flow chart describes the use of a guided search. Upon selecting a guided search as indicated by block 422, in the present embodiment of the invention, the user will be presented with a user interface as shown in FIG. 6. The user at block 424 will then select the plant group from which the user will be prompted for further identifying features. FIG. 6 shows that the images of each plant group is presented in the user interface.

At block 426, the user will be prompted by a combination of text and images displayed in two or more windows as illustrated in 342 and 344 in FIG. 7. The user can perform searches will simultaneously referring to visual aids such as but not limited to images in window 344. Thus searches are conducted while referring to the visual aids presented on the same screen, and any text searches are toggled to accompanying and informative visual aids. In the present embodiment, the user navigates through the plant family via both photographs and text. This greatly simplifies the search process for novice users. The present invention uses images to verify text-based traits at each point along the search. At block 428, the user continues to narrow down the possibilities through the options presented on the screen.

Referring now to block 430 in FIG. 13, it should be understood that although the primary system is photo-driven, it is possible for an advanced user to skip ahead in the search process using the text window 342. FIG. 8 shows the window 344 with the options available to user for selection. Although not shown, some embodiments of the present invention may also have the text window 342 displayed on the screen in FIG. 8.

Block 432 shows that thumbnail images may be presented at the end of a search. Block 434 shows that the image may be enlarged to provide more detailed viewing. The image may then be saved to file if desired. In some embodiments, the user may be presented with the opportunity to purchase the plant if available. The user may click on a link that brings the user to a merchant site or to an online store on the internet, or to other sites contqining additional information about the care, distribution or habit of the plant species.

It should also be understood that a user can access a glossary without losing the current search, as this feature is accessed through a separate mode.

Figure 14:
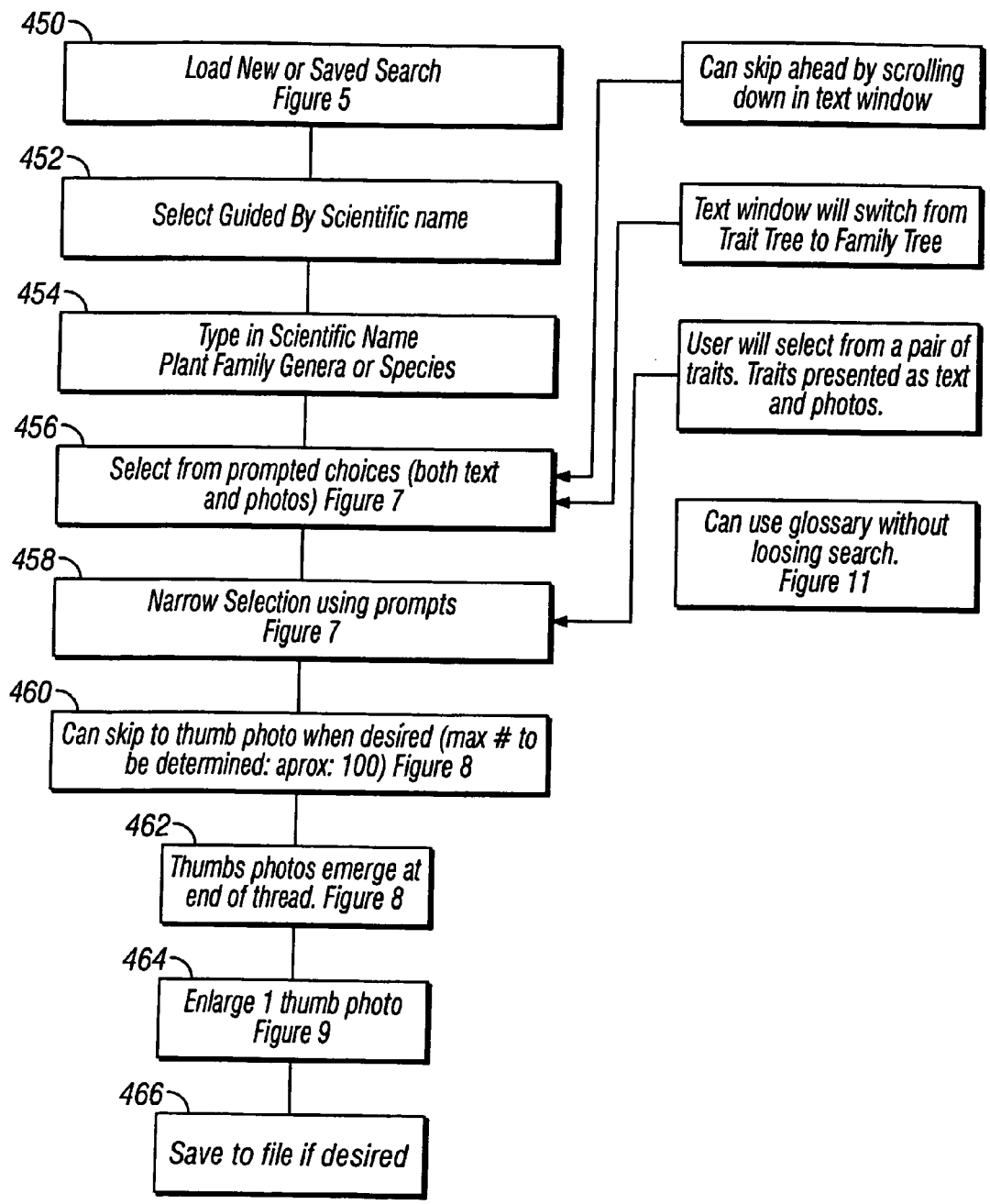

Referring now to FIG. 14, one embodiment of the process for conducting a search using a scientific name will now be described. Block 450 shows that user may opt for a new search or load a saved search. Block 452 shows that in this example, the user has selected a search by scientific name. Block 454 shows that the user may opt to enter a variety of key words such as but not limited to scientific name, plant family, genera, or species. These key words may be entered in a text box as shown in FIG. 5. Block 456 shows that the user will be prompted by a combination of text and images displayed in the two windows 342 and 344 in FIG. 7. The user can perform searches while simultaneously referring to visual aids such as but not limited to images in window 344. At block 456, the advanced user may opt to skip ahead by scrolling down in text window 342. Block 456 also shows that the text window will switch from Trait Tree to Family Tree. At block 458, the user continues to narrow down the possible plant matches through the options presented on the screen. At block 458, the user will select from a list of Genera, than a list of species.

Block 460 shows that the user can skip through thumbnail images of the possible plant possibilities. Block 462 shows that thumbnail photos emerge at the end of the thread. Thus in some embodiments, the search will eventually reach a point where the search has narrowed the candidates down so that the only images that are presented are views of the apical complex of the possible plants. The present invention will then do the final sorting based on comparison and/or identification of traits found on the apical complex views. This type of search where the final identification step is based on apical views may yield more accurate results. Furthermore, embodiments of the present invention may use fewer steps to reach a plant identification since traits not relevant to narrowing traits found on apical views are not presented to the user. Only those questions useful for narrowing traits on apical views will be asked. Block 464 shows that the user may enlarge a thumbnail photo of the identified plant and save the file if desired at 466.

Figure 15:
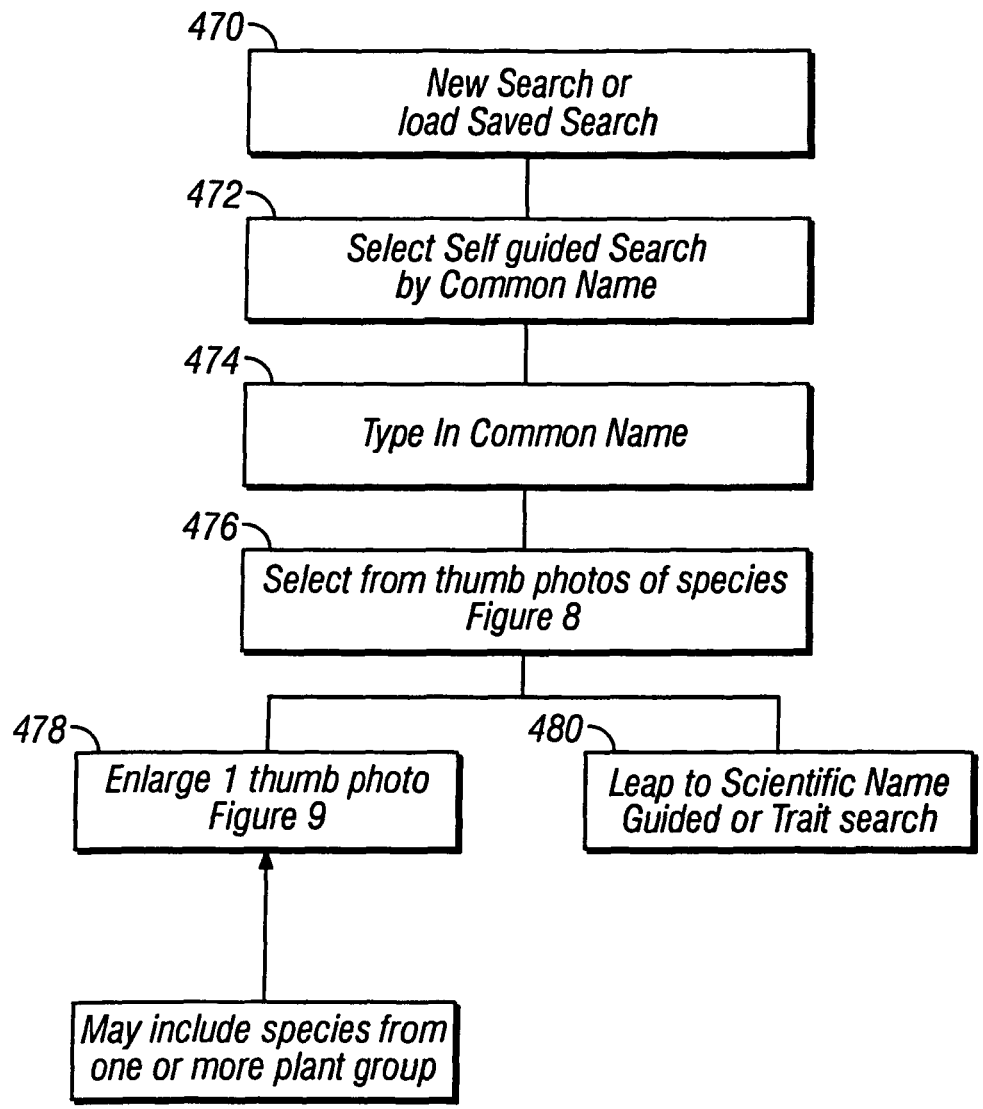

Referring now to FIG. 15, a search conducted based on common name will now be described. Again, block 470 shows that the user may start with a new search or a saved search. Block 472 shows the user selects a self-guided search by common name. Block 474 shows that the user may type the common name to conduct the search. At this and other similar points, a spell check feature may be activated as a search aid. Block 476 shows that the user may select thumbnail images of various plant species. By way of example and not limitation, FIG. 8 shows the images that may be presented to the user at block 476. The user may opt to enlarge one of the images as indicated in block 478 or the user may opt to advance to another search page using one of the other search types such as but not limited to scientific name, guided, or trait search.

Figure 16:
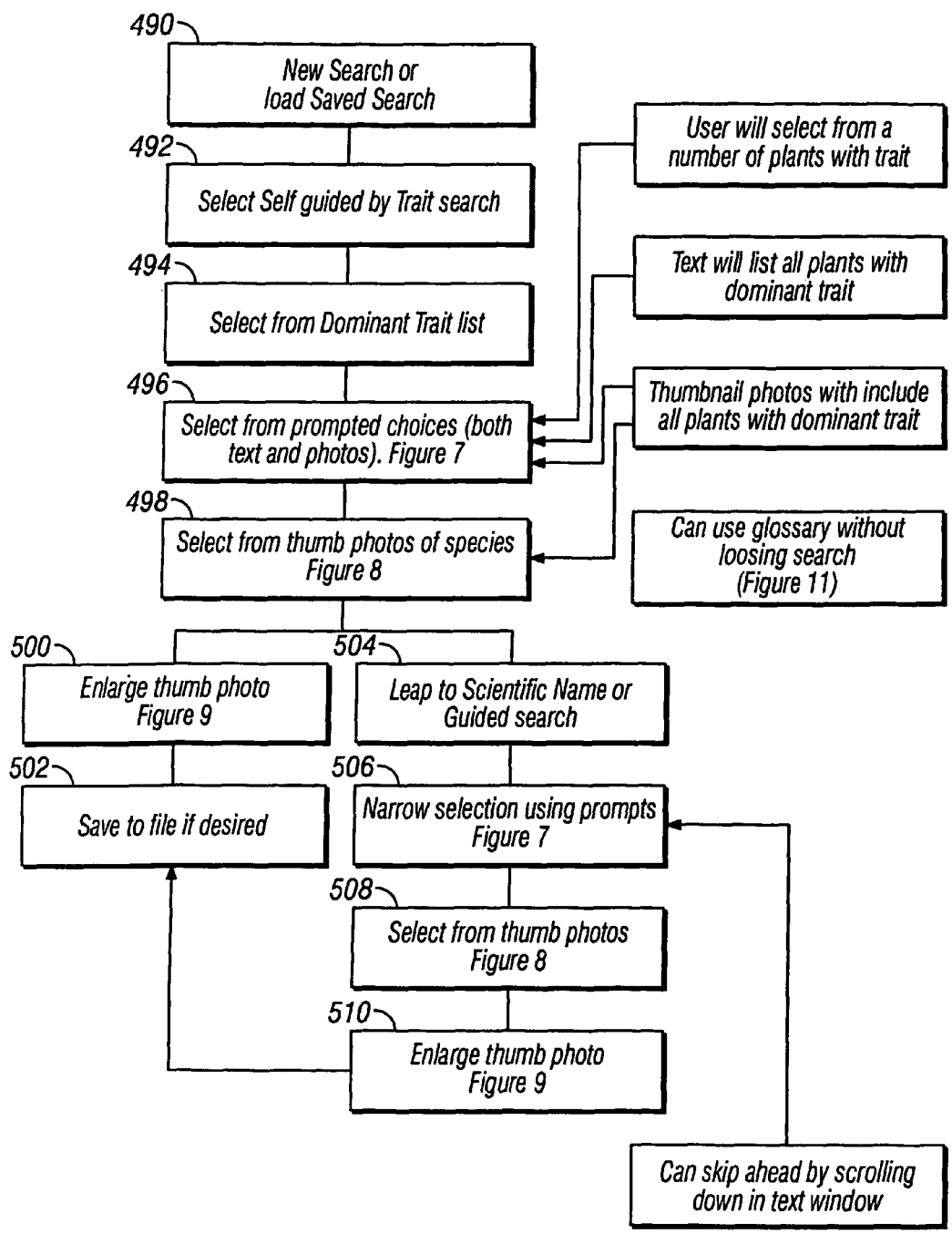

Referring now to FIG. 16, one embodiment of a self-guided search by trait will now be described. Block 490 again shows that the user may opt to load a saved search. Block 492 shows that the user may select a self-guided by trait search. Block 494 shows that the user may initiate the search by selecting from the dominant trait list. The lower half of block 342 on screen shot in FIG. 7 shows this. Block 496 shows that user will be guided by a variety of text and image prompts to narrow the possible matches (see FIG. 7). User will select from a number of plants with trait. Text will list all plants with dominant trait. Block 498 shows that the user may then select the appropriate matches based on the users selection of thumb photos in FIG. 8. Thumbs will include all plants with dominant trait. Block 500 shows that the user may enlarge a match image (FIG. 9) and that the information presented (and the search) may be saved as indicated in block 502. Alternatively, as indicated by block 504, the user may opt to further narrow the search using a scientific name or guided search. Block 506 indicates that the user may be prompted to narrow the search based on images and text combinations (FIG. 7). Block 508 shows that the user may enlarge a match image (FIG. 9) and that the information presented (and the search) may be saved as indicated in block 510.

It should be understood that prior to reaching the interface for searches shown in FIG. 5, a user login may be used to limit access to only those users with accounts or who have paid to use the service. The service may be provided through a web interface or may be run as a client running off a local computer owned by the user.

Figure 17:
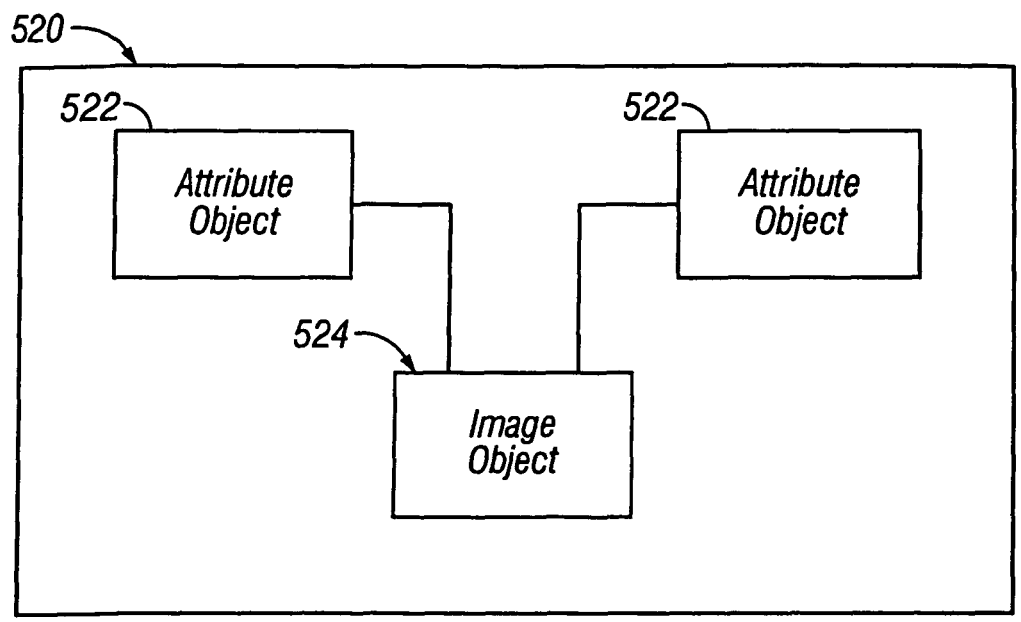
FIG. 17 shows a data structure according to the present invention.

FIG. 17 shows that in one embodiment of the present invention, a data structure in a datastore 520 is provided. The data structure includes information resident in a database used by the application program and includes a plurality of attribute data objects 522 and at least one image object 524. The plurality of attribute data objects containing different information. The data objects may contain information that is linked to another database. The plurality of image objects may contain images of apical complex of plant species and each of the image objects have a linked relationship to at least one of the attribute data objects, wherein the images are created based on a standard for distance and other features.

Figure 18:
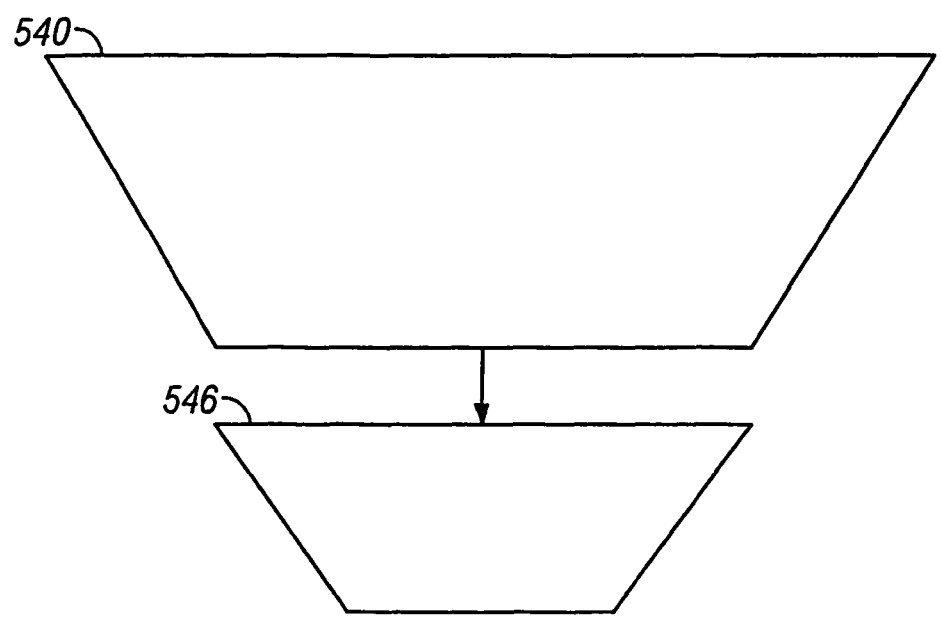
FIG. 18 shows a schematic describing how a search in one embodiment of the present invention is organized.

Referring now to FIG. 18, a graphic representation is shown of one method of guiding a user in one embodiment of a plant identification system according to the present invention. FIG. 18 shows that the initial questions represented by funnel 540 will ask the user to select characteristics of their unknown plant that will narrow down the possible matches in the apical view portion of the search. In the portion of the search represented by funnel 546, the search is driven by trait clusters found on the apical view of each potential matching plant. The user will continue to be queried on trait characteristics found from viewing the apical complex of the plant until a match is found. Thus, the search of the present invention may start broadly, asking questions about the plant generally, but the final matching will be accomplished based on traits found on the apical complex. This type of search strategy (where the user always does final comparisons based on the apical complex) generally reduces the number of steps to reach a match. The matches are also of higher accuracy since the final matches may use apical complex images created using a standardized capturing methodology.

Figure 19:
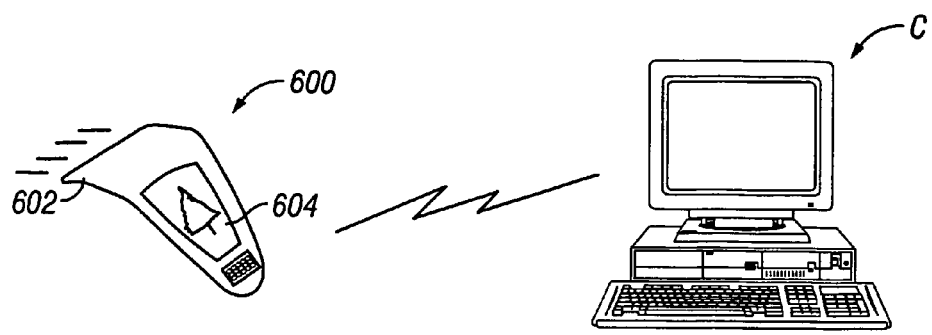
FIG. 19 shows a handheld device according to the present invention.

Referring now to FIG. 19, with any of the embodiments above, a hand-held inventory product 600 containing this identification system may be used. The hand-held bar-code inventory systems may be used by commercial nurseries as an identification device. Some embodiments may have an infrared bar code reader 602 to read identification. The information is then transmitted to a computer C by either wired or wireless means. Others may optionally, have a screen 604 to show images of the plant. The screen may be touch sensitive to allow a user to select between different options presented to the user to identify the plant. A miniature keyboard or other buttons may also be included to allow for entry of data.

Figure 20:
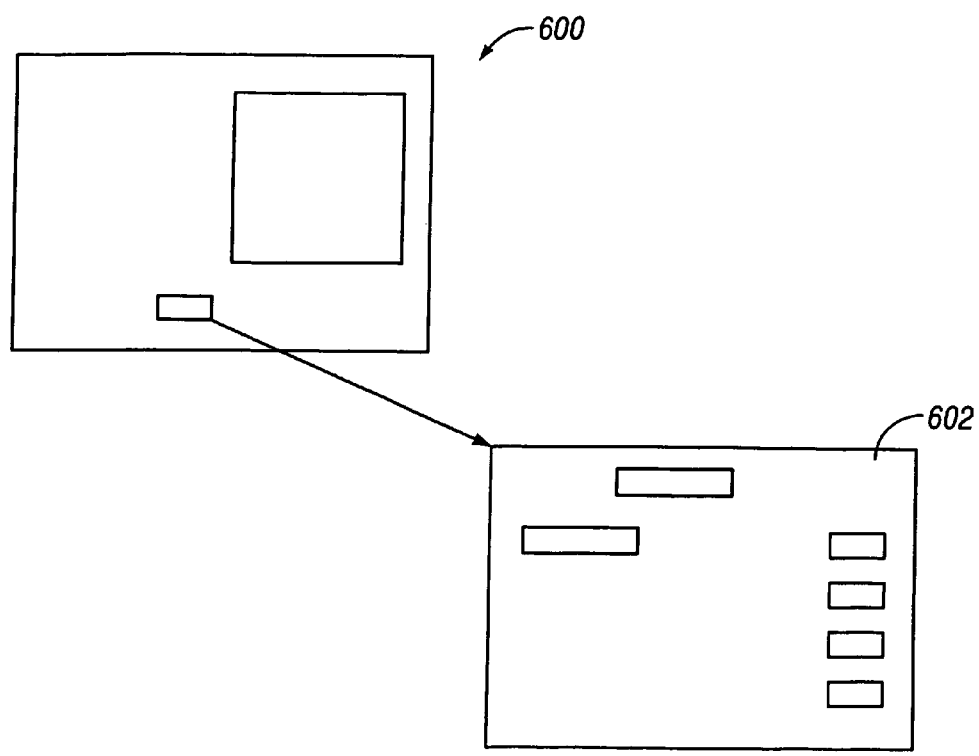
FIG. 20 shows an E-commerce system according to the present invention.

Referring now to FIG. 20, the user may also be presented with options to purchase particular plants from the client or from the website. As seen in FIG. 20, after a plant has been identified in screen shot 600, there may be link or button that may lead to another screen 602 that allows a user to purchase the plant identified. The link may lead to the same website or it may lead to an affiliate website that sells the desire plant.

Although the invention has been described herein with reference to specific embodiments, conceivably, many modifications and variations therein will readily occur to those skilled in the art. The preferred embodiments are disclosed and described in detail and are as exemplary and is therefore not intended to be limiting of the invention. Accordingly, all such variations and modifications are included within the intended scope of the invention. With any of the embodiments above, a hand-held inventory product containing this identification system may be used. The hand-held bar-code inventory systems may be used by commercial nurseries as an identification device. The present system may provide a plurality of search options (guided). Some of these are nested searches. With any of the embodiments above, the present application may be implemented within a framework of an Application Service Provider (ASP), embedded in a central computer platform, and accessible to users over a data communication network, such as but not limited to the Internet or Intranet. The ASP approach imparts the application the ability to establish a plant species data warehouse, which enables a continuous and updating of plant species in the database, and allows users to access the large database without requiring the user to store the images on their local machines. Some embodiments may of course, store image to the local drive if desired by the user.

The publications discussed or cited herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. All publications mentioned herein are incorporated herein by reference to disclose and describe the structures and/or methods in connection with which the publications are cited. For example, U.S. Provisional Application No. 60/530,359 (Attorney Docket No. 95545-0001) filed Dec. 16, 2003 is incorporated herein by reference for all purposes.

Expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A process for identifying unidentified plants comprising:
    (A) obtaining a sample or image of the apical complex of an unidentified plant and identifying at least one distinguishing characteristic of the apical complex typical of the unidentified plant;
    (B) comparing on a computing machine the distinguishing characteristic of the apical complex with a database of at least one plant genus comprising
        (1) a plurality of images of distinguishing characteristics of apical complexes for each plant sufficient to distinguish each plant species from all other plant species within the genus; and
        (2) text data corresponding to said distinguishing characteristics of apical complexes for each plant;
    wherein substantially every plant in said database is represented by at least one image of distinguishing characteristics of apical complexes sufficient to enable identification of the plant species within the genus;
    (C) correlating on said computing machine the distinguishing characteristic of the apical complex of the unidentified plant with distinguishing characteristics of the apical complexes of known and identified plants in said database; and
    (D) repeating step (C) for a second and subsequent distinguishing characteristic until a sufficient number of the distinguishing characteristics of the apical complex have been ascertained to correlate the apical complex of the unidentified plant with said plants in said database,
    (E) assigning the unidentified plant to a plant genus and/or genus with similar distinguishing characteristic of the apical complex, and
    (F) displaying the results of step E to a user on a graphics display device.

2. The process of claim 1, wherein information comprising the identified plant species, genus, distinguishing characteristics and the image of the plant are stored in the database.

3. The process of claim 2, wherein the information in said database is stored in a format searchable in response to a specific query in order to identify the specific plant or plants in said database that satisfy the characteristic of the query criteria.

4. The process of claim 1, wherein the unidentified plant is a vascular plant.

5. The process of claim 1, wherein the process of identifying a plant employs a software algorithm.

6. The process of claim 5, wherein the software driven identification process uses guided text with complementary visual images.

7. The process of claim 1, wherein the process of comparing and matching the distinguishing characteristics of the apical complex uses a search engine.

8. The process of claim 1, wherein the process of comparing the distinguishing characteristics of the apical complex employs dichotomous keys that are based on physical attributes of said known and identified plants or on plant morphology.

9. The process of claim 1, wherein the images are black-and-white or color.

10. The process of claim 1, wherein the database is compiled by a process comprising:
    (A) locating a stem and/or branch apical complex of a particular plant;
    (B) obtaining a particular image of the particular plant's distinguishing characteristics and the distinguishing characteristics of the apical complex with sufficient resolution to distinguish among the different plant species in said database;
    (C) correlating said particular image with unique identification information corresponding to the species of the particular plant, said unique identification information comprising the particular plant's distinguishing characteristics and the particular plant's genus and species; and
    (D) storing said particular image and identification information in a database.

11. A plant identification system comprising:
    a client running on a local computer;
    a server;
    said client configured to communicate with the server and cause the local computer to display a user interface;
    said server having a processor with logic to process input from the user and send image data to the client for display to the user;
    wherein said processor comprises instructions for running the steps of the method as set forth in claim 6 to guide the user to identify an unidentified plant.

12. The device of claim 11, wherein image data is stored on the server.

13. The device of claim 11, wherein a portion of the image data is stored by the client on the local computer.

14. A computer program product for use with a graphics display device, said computer program product comprising a nontransitory computer readable medium comprising:
    a database of at least one plant genus, said database comprising:
        (1) a plurality of images of distinguishing characteristics of apical complexes for each plant sufficient to distinguish each plant species from all other plant species within the genus; and
        (2) text data corresponding to said distinguishing characteristics of apical complexes for each plant;
    wherein every plant in said database is represented by at least one image of distinguishing characteristics of apical complexes sufficient to enable identification of the plant species within the genus;
    computer readable program code for causing a computer to display a user interface;
    computer readable program code for prompting a user to select among images of plant traits, said images shown on the graphics display device;
    computer readable program code displaying text linking attribute information to images of plant traits;
    computer readable program code for prompting the user to identify a distinguishing characteristic of the apical complex typical for an unknown plant and correlating the distinguishing characteristic of the apical complex with distinguishing characteristic of the apical complex of a known and identified plant from said database; and
    computer readable program code for the prompting step for a second and subsequent distinguishing characteristics of the apical complex until a sufficient number of the distinguishing characteristics of the apical complex have been ascertained to correlate the apical complex with the apical complex of a known and identified plant from said database;
    said prompting of a user being implemented via said graphics display device; and
    wherein the results of the correlation are displayed on said graphics display device.

15. A process for compiling a database of a plant genus for the identification of plants, comprising:
   (A) locating a stem and/or branch apical complex of a particular plant;
   (B) obtaining an image of the particular plant's distinguishing characteristics and the distinguishing characteristics of the apical complex of the particular plant with sufficient resolution to distinguish among the different plant species within said plant genus;
   (C) correlating said image with unique identification information corresponding to the species of the particular plant, said unique identification information comprising the particular plant's distinguishing characteristics and the particular plant's genus and species;
   and (D) storing said image and identification information in a database stored in a computer-readable memory, and further wherein said image and identification information are displayed on a graphics display device in response to a specific query;
   wherein substantially every plant in said database is represented by at least one image of distinguishing characteristics of apical complexes sufficient to enable identification of the plant species within the genus.

16. The process of claim 15, wherein said image is a photographic image.

17. The process of claim 15, wherein Step (B) further comprises obtaining longisectional images of the apical complex.

18. The process of claim 15, wherein the apical complex of the plant shows at least one growth cycle.

19. A computer implemented method for plant identification, the method comprising:
   providing a database of at least one plant genus comprising
      (1) a plurality of images of distinguishing characteristics of apical complexes for each plant sufficient to distinguish each plant species from all other plant species within the genus; and
      (2) text data corresponding to said distinguishing characteristics of apical complexes for each plant;
   wherein every plant in said database is represented by at least one image of distinguishing characteristics of apical complexes sufficient to enable identification of the plant species within the genus;
   providing a user interface;
   displaying on the user interface, a first set of text prompts and image prompts from the database;
   receiving the user selection;
   processing the user selection based on a decision tree and presenting a second set of text prompts and image prompts from the database based on the user selection;
   receiving the user selection from the second set of text prompts and image prompts;
   repeating the displaying, receiving, and processing until the user is presented with images of apical views of trait clusters; and
   narrowing possible plant matches based on traits shown on the apical views, wherein said traits are sufficient to enable identification of each plant species within the genus,
   wherein all method steps are performed on a computer or a network of computers.

20. A computer program product comprising
   nontransitory computer readable memory for storing data for access by an application program being executed on a computer;
   a data structure in said memory, said data structure including information resident in a database used by the application program and including:
   a plurality of attribute data objects stored in said memory, each of said attribute data objects containing different information from said database;
   a plurality of image objects, wherein said image objects contain images of apical complexes of plant species sufficient to enable identification of each plant species within the genus, and wherein each of the image objects have a linked relationship to at least one of said attribute data objects; and
   wherein said attribute data objects and said image objects are displayed on a graphics display device in response to a specific query; and
   wherein substantially every plant in said database is represented by at least one image of distinguishing characteristics of apical complexes sufficient to enable identification of the plant species within the genus.

21. A system to aid in a visual plant identification process, comprising:
   an image database containing a plurality of images of apical complexes of plants sufficient to enable identification of each plant species within the genus;
   a knowledge database, cross-referenced to said image database, for the purpose of assisting in the identification of plants;
   a user-interface to solicit, from a user in a sequential manner, a plurality of descriptive traits of an unknown plant for identification; and
   a processor comprising a diagnostic engine, responsive to each of said traits, wherein said traits of the unidentified plant are employed by said engine to identify, from a plurality of possible matches, a subset of matches that are consistent with the traits; and using the subset of matches, reorganizing an information space of said image database for concurrent presentation of a plurality of images for user review via the user-interface;
   wherein the user-interface is configured to continue to solicit descriptive traits based on the new subset of matches until the traits to be processed by the diagnostic engine only relate to the features found on the apical complex of the unidentified plant;
   wherein the user-interface is configured to continue soliciting distinguishing characteristics until a sufficient number of the distinguishing characteristics of the apical complex have been ascertained to correlate the apical complex with one of the known plant species.

22. A method for aiding a visual plant identification process, comprising:
   creating an image database from a collection of plant images pertaining to plant species with at least one apical view of each plant species sufficient to enable identification of each plant species within the genus;
   creating a knowledge database with text keys to distinguishing characteristics of the apical complex visible in the apical view of the plant species, wherein said knowledge database is cross-referenced to said image database, for the purpose of assisting in the identification process;
   collecting from a user, through a user-interface, one descriptive characteristic of an unknown plant to be identified;
   in response to said descriptive characteristic, identifying, from a plurality of possible matches included within the knowledge database, a subset of matches consistent with the descriptive characteristic input by the user;

repeating the collecting step to continue soliciting descriptive characteristics until a sufficient number of the distinguishing characteristics of the apical complex have been ascertained to correlate the apical complex of said unknown plant with a subset of matches less than approximately 100;

using the subset of matches, reorganizing an information space of said image database for concurrent presentation of a plurality of images related to the descriptive characteristics for user review via the user-interface wherein all method steps are performed on a computer or a network of computers.

23. A computer implemented method for plant identification, the method comprising:
providing a user interface;
providing a text and image guided search of a database of at least one plant genus, said database comprising:
(1) a plurality of images of distinguishing characteristics of apical complexes for each plant sufficient to distinguish each plant species from all other plant species within the genus; and
(2) text data corresponding to said distinguishing characteristics of apical complexes for each plant; wherein every plant in said database is represented by at least one image of distinguishing characteristics of apical complexes sufficient to enable identification of the plant species within the genus; displaying before the user a screen with a plurality of matched text and images; navigating a decision tree and presenting a second criteria based on the user's response;
continuing until apical views of possible matches are displayed, wherein said apical views are sufficient to enable identification of each plant species within the genus; and
determining matches based on traits found on apical views wherein all method steps are performed on a computer or a network of computers.

24. A computer program product for use with a graphics display device, said computer program product comprising:
a nontransitory computer readable medium, said computer readable medium storing a database containing a plurality of image objects, each image object containing at least one view of the apical complex for each plant species in the database sufficient to enable identification of each plant species within the genus; and
program code comprising instructions for causing a computer to display said image objects on a graphics display device in response to a specific query.

25. The computer program product of claim 24, wherein each image object contains at least one distinguishing characteristic of the apical complex of a plant species; and wherein said database also contains a plurality of attribute objects, each attribute object describing one of the distinguishing characteristics present in each image object.

\* \* \* \* \*